(12) United States Patent
Alshibl et al.

(10) Patent No.: US 10,730,885 B1
(45) Date of Patent: Aug. 4, 2020

(54) COUMARIN DERIVATIVES

(71) Applicant: KING SAUD UNIVERSITY, Riyadh (SA)

(72) Inventors: Hanan M. Alshibl, Riyadh (SA); Ebtehal S. Al-Abdullah, Riyadh (SA); Mogedda E. Haiba, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/399,950

(22) Filed: Apr. 30, 2019

(51) Int. Cl.
*C07D 493/04* (2006.01)
*A61P 31/04* (2006.01)
*A61P 29/00* (2006.01)
*C07D 311/12* (2006.01)

(52) U.S. Cl.
CPC ............ *C07D 493/04* (2013.01); *A61P 29/00* (2018.01); *A61P 31/04* (2018.01); *C07D 311/12* (2013.01)

(58) Field of Classification Search
CPC ...... C07D 493/04; C07D 311/12; A61P 29/00; A61P 31/04
See application file for complete search history.

(56) References Cited

U.S. PATENT DOCUMENTS

| | | | |
|---|---|---|---|
| 5,663,375 | A | 9/1997 | Brunacs et al. |
| 7,098,340 | B2 | 8/2006 | Du et al. |
| 8,143,428 | B2 | 3/2012 | Reddy et al. |
| 8,278,465 | B2 | 10/2012 | Iikura et al. |
| 8,569,378 | B2 | 10/2013 | Sakai et al. |
| 8,716,319 | B2 | 5/2014 | Abelman et al. |

OTHER PUBLICATIONS

Nagabhushana, H.,"α-Fe2O3 nanoparticles: An efficient, inexpensive catalyst for the one-pot preparation of 3, 4-dihydropyrano [c] chromenes." Chinese Chemical Letters 22.2 (2011): 143-146.*
Khorassani et al., "Full kinetics and a mechanistic investigation of three-component reaction catalyzed by sodium acetate leading to 3,4-dihydropyrano [c] chromene", Research on Chemical Intermediates (2015), vol. 41, Iss. 8, pp. 5821-5837 (Abstract only).
Kaur et al., "Screening of a library of 4-aryl/heteroaryl-4H-fused pyrans for xanthine oxidase inhibition: synthesis, biological evaluation and docking studies", Medicinal Chemistry Research (2015), vol. 24, Iss. 8, pp. 3334-3349 (Abstract only).
Haiba et al., "Inhibitory activity of benzo [h] quinoline and benzo [h] chromene in human glioblastoma cells", Tropical Journal of Pharmaceutical Research (2016), vol. 15, No. 11, pp. 2337-2343.
Shaikh et al., "Novel task-specific ionic liquid [Et2NH(CH2)2CO2H]{AcO} as a robust catalyst for the efficient synthesis of some pyran-annulated scaffolds under solvent-free conditions", Research on Chemical Intermediates, (2018), vol. 45, No. 3, pp. 1595-1617 (Abstract only).

* cited by examiner

Primary Examiner — John M Mauro
(74) Attorney, Agent, or Firm — Richard C. Litman; Nath, Goldberg & Meyer

(57) ABSTRACT

Coumarin derivatives are pyranocoumarins of formula 2 and coumarin-sulfonamides of formula 3, respectively,

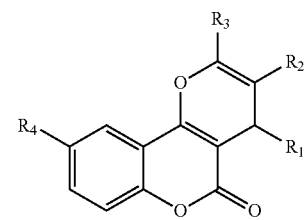

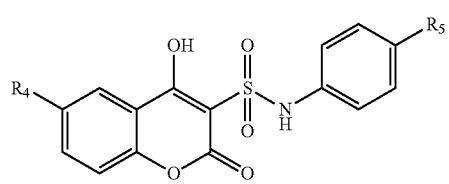

wherein $R_1$ is 4-$NO_2C_6H_4$ or 2-Furyl; $R_2$ is CN or $CONH_2$; $R_3$ is $NH_2$, $NCHN(CH_3)_2$ or $NCHR_6$; $R_4$ is Cl or $CH_3$; $R_5$ is $SO_2NHR_7$, H, OH, $COCH_3$ or $COC_2H_2R_8$; $R_6$ is $C_6H_5$, 3,4,5-$(CH_3O)_3C_6H_2$ or 2,4-$Cl_2C_6H_3$; $R_7$ is H, 1,3-thiazole, or 1,3-diazine and $R_8$ is 4-$O_2NC_6H_4$, 4-$CH_3OC_6H_4$, or 4-$ClC_6H_4$; and pharmaceutically acceptable salts thereof. The coumarin derivatives and pharmaceutical compositions including one or more of such derivatives may by synthesized and used to treat or prevent inflammation or microbial infection, and to reduce levels of reactive oxidative species.

20 Claims, 5 Drawing Sheets

COUMARIN DERIVATIVES

BACKGROUND OF THE INVENTION

1. Field

The disclosure of the present patent application relates to compounds of the coumarin family, and particularly to coumarin derivatives having antioxidant, anti-inflammatory, and antimicrobial activity potentially useful as pharmaceuticals.

2. Description of the Related Art

Therapies with antioxidant, anti-inflammatory and antimicrobial activities hold the potential to effectively treat the majority of diseases. Oxidative stress causes over-production of reactive oxygen species (ROS), which plays an essential role in the pathogenesis of cardiovascular diseases, neurodegenerative diseases, tumor growth and age-related diseases. Inflammatory diseases decrease the quality of life of many patients. However, the current medicinal drugs aimed at combatting inflammatory diseases or treating related symptoms are not always effective and may cause serious adverse effects. Finally, even as infectious diseases are among the world's leading causes of death, antimicrobial resistance has been commonly reported worldwide.

Hence, there is a constant need for developing new compounds having antioxidant, anti-inflammatory and antimicrobial activity for use as pharmaceuticals. Thus, coumarin derivatives solving the aforementioned problems are desired.

SUMMARY

The coumarin derivatives are compounds selected from the group consisting of pyranocoumarins of general formula 2 and coumarin-sulfonamides of general formula 3, respectively,

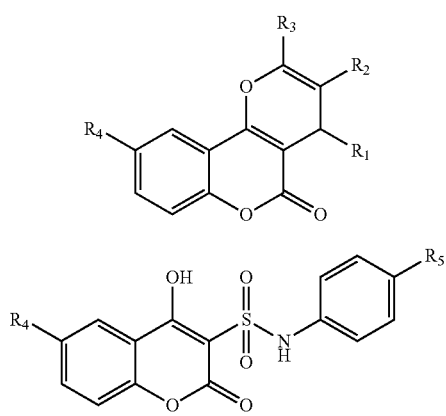

wherein $R_1$ is 4-$NO_2C_6H_4$ or 2-Furyl; $R_2$ is CN or $CONH_2$; $R_3$ is $NH_2$, $NCHN(CH_3)_2$ or $NCHR_6$; $R_4$ is Cl or $CH_3$; $R_5$ is $SO_2NHR_7$, H, OH, $COCH_3$ or $COC_2H_2R_8$; $R_6$ is $C_6H_5$, 3,4,5-$(CH_3O)_3C_6H_2$ or 2,4-$Cl_2C_6H_3$; $R_7$ is one of H, 1,3-thiazole and 1,3-diazine; and $R_8$ is one of 4-$O_2NC_6H_4$, 4-$CH_3OC_6H_4$, and 4-$ClC_6H_4$; and pharmaceutically acceptable salts thereof.

A method of reducing at least one of an inflammatory response, a microbial infection and a level of reactive oxygen species, may include administering to a patient in need thereof at least one of the coumarin derivatives.

A pharmaceutical composition may include non-toxic, inert pharmaceutical suitable excipients, and one or more active compounds including at least one of the coumarin derivatives.

A method of making a pharmaceutical composition may include mixing a coumarin derivative under sterile conditions with a pharmaceutically acceptable carrier and preservatives, buffers, or propellants to create the pharmaceutical composition; and providing the pharmaceutical composition in a form suitable for daily, weekly, or monthly administration. Preferably, the composition is capable of being administered orally.

A method of treating, reducing and preventing inflammation, infection or high ROS levels may include administering to a patient in need thereof a therapeutically effective amount of a pharmaceutical composition prepared as described above.

Exemplary coumarin derivatives (referred to herein alternatively as the pyranocoumarins or coumarin-sulfonamides) were synthesized according to embodiments of the present subject matter and tested for antioxidant and anti-inflammatory activities, as well as antimicrobial activity against medically important bacterial and fungal strains. 4-Hydroxy-6-methylcoumarin and 6-chloro-4-hydroxycoumarin moieties were selected as theoretical pharmacophores for more powerful and efficient antioxidant, antimicrobial and/or anti-inflammatory activities based on structure-function relationships. In addition, the lipophilicity and in silico drug-likeness of the target compounds were assessed.

These and other features of the present disclosure will become readily apparent upon further review of the following specification and drawings.

BRIEF DESCRIPTION OF THE DRAWINGS

Similar reference characters denote corresponding features consistently throughout the attached drawings and description.

DETAILED DESCRIPTION OF THE PREFERRED EMBODIMENTS

Figure 1:
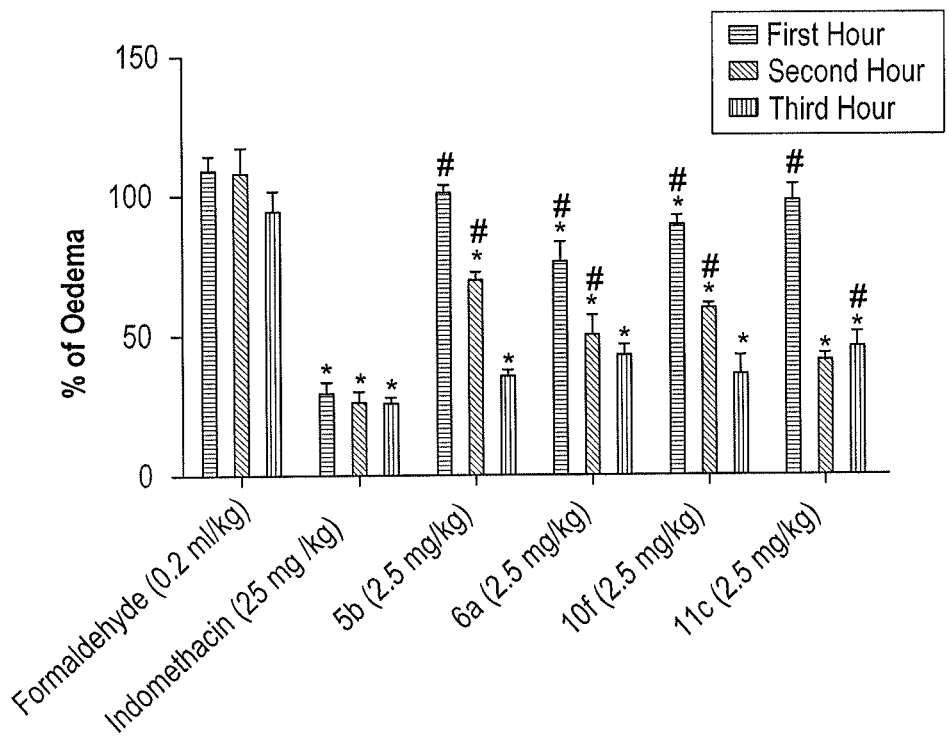
FIG. 1 is a chart reporting the percent of oedema (also spelled edema) in rats pretreated with the control drug indomethacin (25 mg/kg) compared to compounds 5b, 6a, 10f and 11c (2.5 mg/kg), respectively.

Coumarin is a compound found in many plants having the formula:

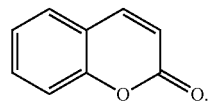

The coumarin derivatives are compounds selected from the group consisting of pyranocoumarins of general formula 2 and coumarin-sulfonamides of general formula 3, respectively,

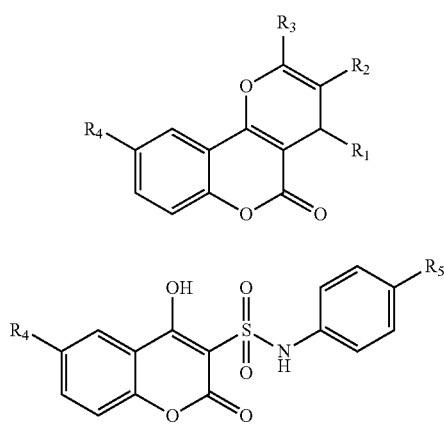

wherein $R_1$ is 4-$NO_2C_6H_4$ or 2-Furyl; $R_2$ is CN or $CONH_2$; $R_3$ is $NH_2$, $NCHN(CH_3)_2$ or $NCHR_6$; $R_4$ is Cl or $CH_3$; $R_5$ is $SO_2NHR_7$, H, OH, $COCH_3$ or $COC_2H_2R_8$; $R_6$ is $C_6H_5$, 3,4,5-$(CH_3O)_3C_6H_2$ or 2,4-$Cl_2C_6H_3$; $R_7$ is H, 1,3-thiazole, or 1,3-diazine; and $R_8$ is 4-$O_2NC_6H_4$, 4-$CH_3OC_6H_4$, or 4-$ClC_6H_4$; and pharmaceutically acceptable salts thereof.

The coumarin derivatives include pyranocoumarin and coumarin-sulfonamide derivatives. The pyranocoumarin derivatives include compounds 5a-b, 6a-b, 7a-b and 8a, 8c-f, having the formulas provided below:

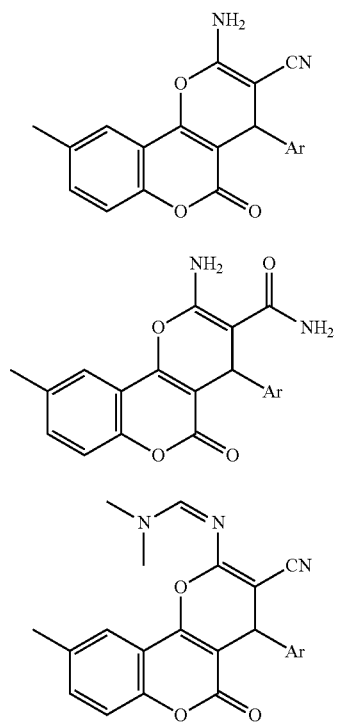

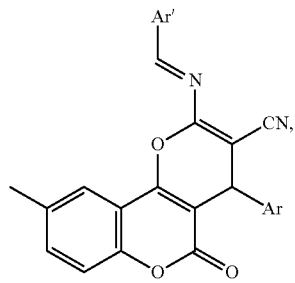

wherein Ar and Ar' are shown in the following Table 1:

TABLE 1

| Pyranocoumarin derivatives | | |
|---|---|---|
| Comp. No. | Ar | Ar' |
| 5a | 4-$NO_2C_6H_4$ | — |
| 5b | 2-Furyl | — |
| 6a | 4-$NO_2C_6H_4$ | — |
| 6b | 2-Furyl | — |
| 7a | 4-$NO_2C_6H_4$ | — |
| 7b | 2-Furyl | — |
| 8a | 4-$NO_2C_6H_4$ | $C_6H_5$ |
| 8c | 4-$NO_2C_6H_4$ | 3,4,5-$(OCH_3)_3C_6H_2$ |
| 8d | 2-Furyl | 3,4,5-$(OCH_3)_3C_6H_2$ |
| 8e | 4-$NO_2C_6H_4$ | 2,4-diCl$C_6H_3$ |
| 8f | 2-Furyl | 2,4-diCl$C_6H_3$ |

The coumarin-sulfonamide derivatives include compounds 10a-f, 11a-f, and 12a-f, having the formulas provided below:

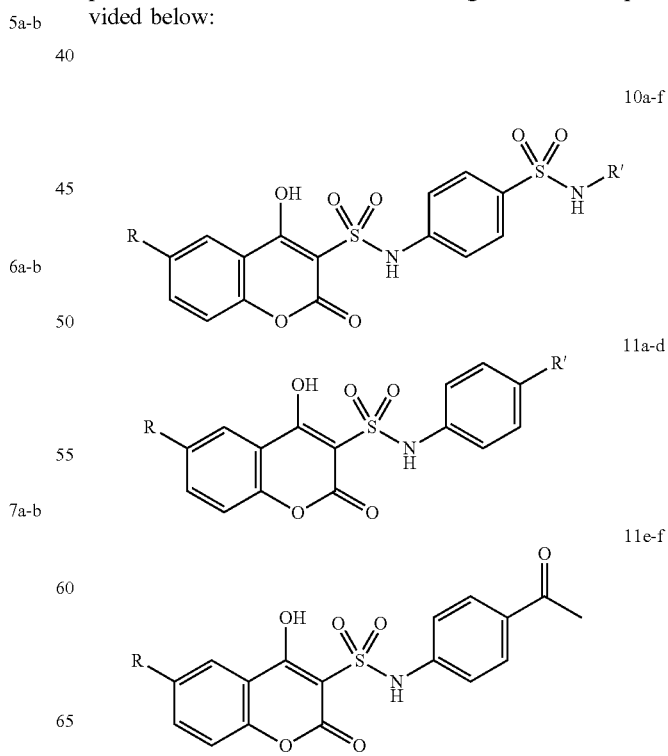

-continued

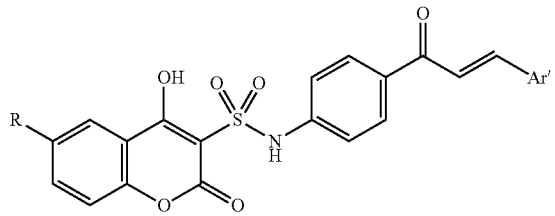

12a-f wherein R, R' and Ar' are shown in the following Table 2:

TABLE 2

| Comp. No. | Coumarin sulfonamides R | R'/Ar' |
|---|---|---|
| 10a | Cl | H |
| 10b | $CH_3$ | H |
| 10c | Cl | pyrimidin-2yl |
| 10d | $CH_3$ | pyrimidin-2yl |
| 10e | Cl | thiazol-2-yl |
| 10f | $CH_3$ | thiazol-2-yl |
| 11a | Cl | H |
| 11b | $CH_3$ | H |
| 11c | Cl | OH |
| 11d | $CH_3$ | OH |
| 11e | Cl | — |
| 11f | $CH_3$ | — |
| 12a | Cl | $4\text{-}NO_2C_6H_4$ |
| 12b | $CH_3$ | $4\text{-}NO_2C_6H_4$ |
| 12c | Cl | $4\text{-}ClO_6H_4$ |
| 12d | $CH_3$ | $4\text{-}ClO_6H_4$ |
| 12e | Cl | $4\text{-}MeOC_6H_4$ |
| 12f | $CH_3$ | $4\text{-}MeOC_6H_4$ |

The coumarin derivative is at least one of an anti-inflammatory agent, an antimicrobial agent and an antioxidant agent.

A method of treating diseases susceptible to treatment with an anti-inflammatory agent, an anti-microbial agent and an anti-oxidant agent may include administering to a patient in need thereof at least one of the coumarin derivatives disclosed herein.

A pharmaceutical composition may comprise non-toxic, inert pharmaceutically suitable excipients, and one or more active compounds comprising at least one of the coumarin derivative compounds.

The pharmaceutical composition may be in a form suitable for daily, weekly, or monthly administration. Preferably, the pharmaceutical composition is in a form for oral administration. The form of the pharmaceutical composition may be a tablet, pill, capsule, granule, powder, ointment, sterile parenteral solution or suspension, metered aerosol or liquid spray, drops, ampule, injection, teaspoonful, or suppository.

A method of making a pharmaceutical composition includes mixing the coumarin derivative with a pharmaceutically acceptable carrier. For example, the method of making a pharmaceutical composition may include mixing the coumarin derivative under sterile conditions with a pharmaceutically acceptable carrier and preservatives, buffers, or propellants to create the pharmaceutical composition; and presenting the pharmaceutical composition in a form suitable for daily, weekly, or monthly administration.

The composition may be administered orally, nasally, rectally, parenterally, intracisternally, intravaginally, intraperitoneally, topically, transdermally, or by surgical implantation. The composition may be administered in a form selected from liquid oral preparations, solid oral preparations, parenteral preparations, injectable suspensions, and liposomes.

The coumarin derivatives or pharmaceutical compositions can be administered to a subject by any suitable route. For example, the compositions can be administered orally (including bucally and sublingually), nasally, rectally, intracisternally, intravaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body, such as in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

A pharmaceutical composition may include one or more of the coumarin derivatives. To prepare the pharmaceutical composition, one or more of the coumarin derivatives or a salt thereof, as the active ingredient, is intimately admixed with a pharmaceutically acceptable carrier according to conventional pharmaceutical compounding techniques. Carriers may include inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

For parenteral use, the carrier will usually comprise sterile water, though other ingredients, for example, for purposes such as aiding solubility or for preservation, may be included. Injectable suspensions may also be prepared, in which case appropriate liquid carriers, suspending agents, and the like may be employed. Accordingly, the pharmaceutically acceptable carrier can include alcohol, dimethyl sulfoxide (DMSO), a physiological saline, a lipid-based formulation, a liposomal formulation, a nanoparticle formulation, a micellar formulation, a water soluble formulation, a biodegradable polymer, an aqueous preparation, a hydrophobic preparation, a lipid-based vehicle, or a polymer formulation.

The coumarin derivatives also can be administered in the form of liposomes. Liposomes generally are derived from phospholipids or other lipid substances and are formed by mono- or multi-lamellar hydrated liquid crystals dispersed in an aqueous medium. Any nontoxic, physiologically acceptable and metabolizable lipid capable of forming liposomes can be used. The present compositions in liposome form can include, in addition to a compound of the present disclosure, stabilizers, preservatives, excipients, and the like. The preferred lipids are the phospholipids and the phosphatidyl cholines (lecithins), both natural and synthetic.

Pharmaceutical compositions for parenteral injection can include pharmaceutically acceptable sterile aqueous or non-aqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water ethanol, polyols (such as glycerol, propylene glycol, polyethylene glycol, and the like), and suitable mixtures thereof, vegetable oils (such as olive oil), and injectable organic esters, such as ethyl oleate. Proper fluidity can be maintained, for example, by the use of coating materials, such as lecithin, by the maintenance of the required particle size in the case of dispersions, and by the use of surfactants.

The present compositions can include adjuvants, such as preservatives, wetting agents, emulsifying agents, and dispersing agents. Prevention of the action of microorganisms can be ensured by the inclusion of various anti-bacterial and anti-fungal agents, for example, paraben, chlorobutanol, phenol sorbic acid, and the like. It also may be desirable to include isotonic agents, such as sugars, sodium chloride, and the like. Prolonged absorption of the injectable pharmaceutical form can be brought about by the inclusion of agents that delay absorption, such as aluminum monostearate and gelatin. In some cases, in order to prolong the effect of the drug, it is desirable to slow the absorption of the drug from subcutaneous or intramuscular injection. This result can be accomplished by the use of a liquid suspension of crystalline or amorphous materials with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

The present compositions can be in unit dosage forms, such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the coumarin derivative or an amount effective to treat or prevent inflammation, an infection or high levels of ROS may be determined initially from the Examples described herein and adjusted for specific desired coumarin derivatives using routine methods.

The following examples illustrate the present teachings.

Figure 3:
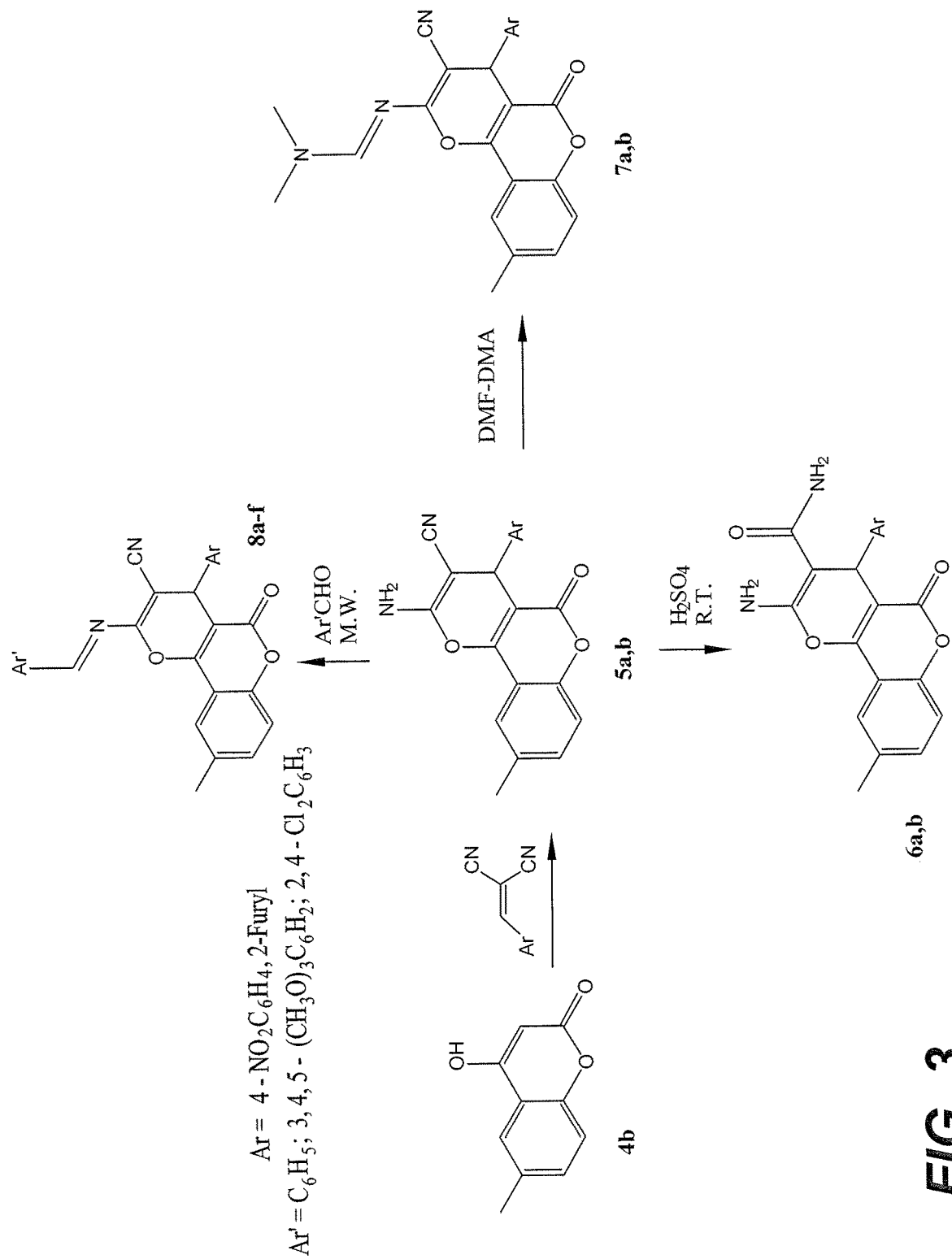
FIG. 3 is a reaction scheme for the synthesis of pyranocoumarins.
Figure 4A:
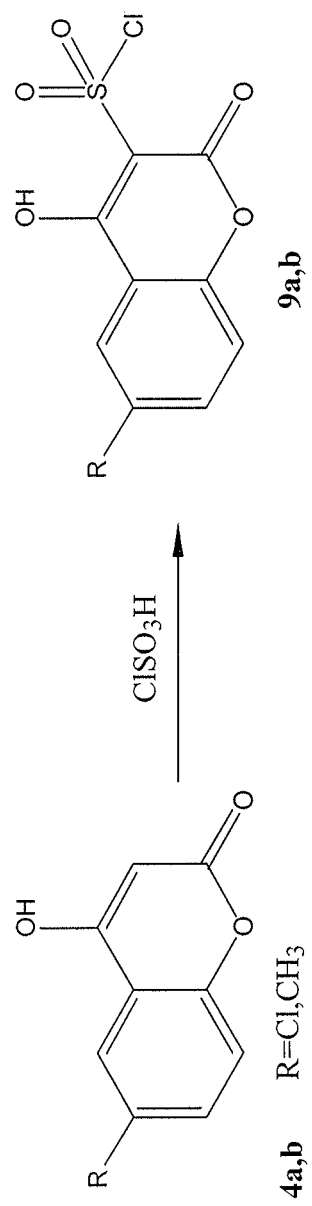
FIGS. 4A, 4B, 4C, and 4D is a reaction scheme for the synthesis of coumarin sulfonamides.
Figure 4B:
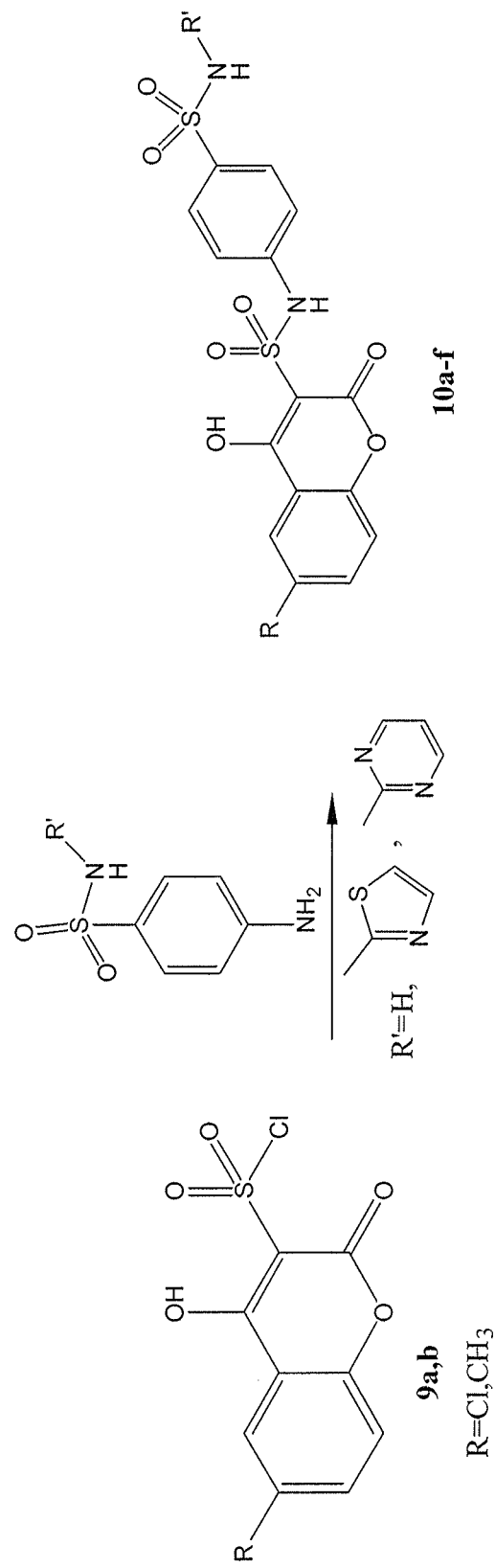
Figure 4C:
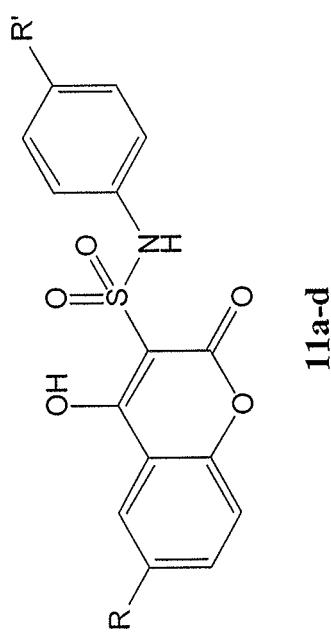
Figure 4C:
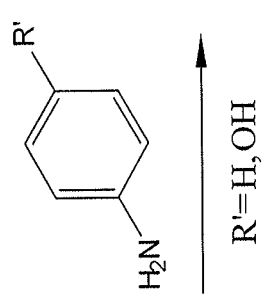
Figure 4C:
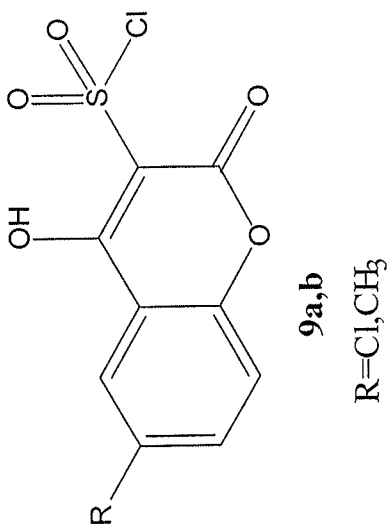
Figure 4D:
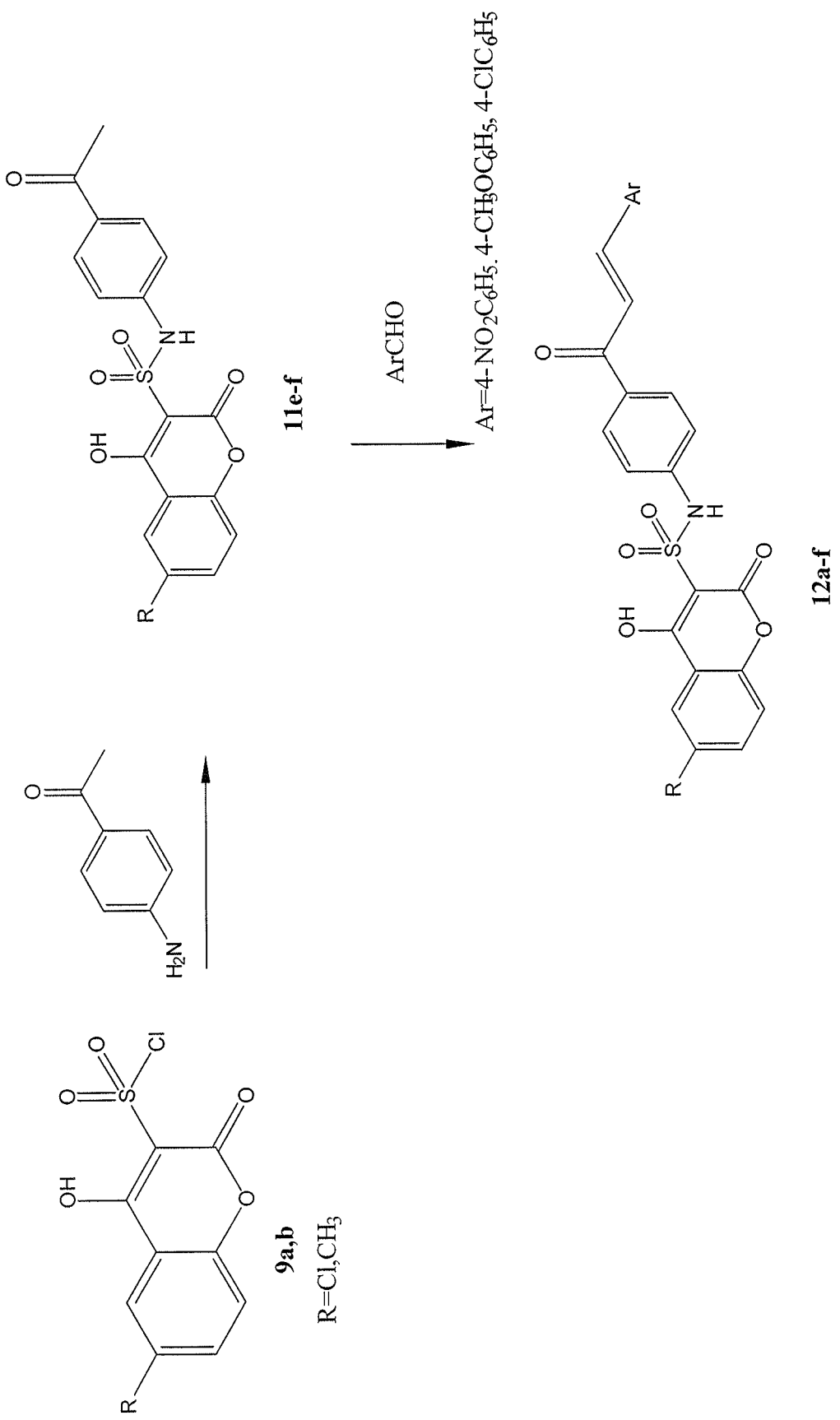

As will be shown, exemplary coumarin derivatives were synthesized and their biological activities as anti-inflammatory, antimicrobial, and antioxidant agents were assessed. Pyranocoumarin and coumarin sulfonamide derivatives prepared according to schemes 1 and 2 are described herein. Synthetic scheme 1, shown in FIG. 3, is a procedure for preparation of the pyranocoumarin compounds having general formula 2. The pyranocoumarins 5a-b were prepared in high yields according to a previously reported method (Kiyani and Ghorbani, "Efficient tandem synthesis of a variety of pyran-annulated heterocycles, 3,4-disubstituted isoxazol-5(4H)-ones, and α,β-unsaturated nitriles catalyzed by potassium hydrogen phthalate in water", *Res Chem Intermed* 41, 7847-7882, 2015). Carboxamide derivatives 6a-b were obtained in good yields through acidic hydrolysis of 5a or 5b, respectively. The reaction of 5a-b with excess N,N-dimethylformamide-dimethylacetal (DMF-DMA) at 100° C. yielded the corresponding derivatives 7a-b within 15-40 minutes. Microwave irradiation was used to obtain the target derivatives 8a-f by treatment of 5a-b with different aromatic aldehydes in 1,4-dioxane. Optimized irradiation time using a microwave synthesizer (e.g., Biotage® Initiator+ microwave, 400 W) was found to be 90 to 110 minutes for this reaction. The products were therefore obtained in short reaction time without use of a hazardous catalyst at yields of 17-37%, except compound 8f, which was obtained at a yield of <6%.

Synthetic scheme 2, shown in FIGS. 4A-4D, is a procedure for preparation of coumarin-3-sulfonamide compounds. Coumarin sulfonyl chlorides 9a-b were prepared by treating the 4-hydroxy-6-substituted coumarins 4a or 4b with chlorosulfonic acid in dichloromethane at 0° C., resulting in high yields of ≥97%. The coumarin-3-sulfonamides were generally obtained either by using a Knoevenagel type of condensation reaction or through condensation of coumarin-3-sulfonyl chlorides with aromatic amines. Preparation of corresponding coumarin-3-sulfonamides 10a-f was achieved by refluxing a preferably equimolar quantity of 9a or 9b with a sulfa-drug in absolute ethanol. Reaction of 9a or 9b with a nucleophilic reagent, aniline or p-substituted aniline, in absolute ethanol under reflux produced corresponding coumarin-3-sulfonamides 11a-f in yields of 48-92%. Claisen-Schmidt condensation of p-acetyl derivatives of 4-hydroxy-6-(substituted)coumarin-3-sulfonamides 11e or 11f with the p-substituted aromatic aldehyde through the addition of sodium hydroxide solution in ethanol at room temperature resulted in corresponding coumarin-sulfonamide chalcone derivatives 12a-f at yields of 15-35%.

Example 1

General Synthesis Procedures

Scheme 1, shown in FIG. 3, and Scheme 2, shown in FIGS. 4A-4D, depict the methods of synthesizing the present coumarin derivatives. The starting material 4-hydroxy-6-methylcoumarin 4b was synthesized according to the method reported by Shah et al., "Communication-New Synthesis of 4-Hydroxycoumarins". *J. Org. Chem.* 25, 677-678 (1960). The other starting material 6-chloro-4-hydroxycoumarin 4a was obtained commercially from Sigma Aldrich (St. Louis, USA). All other reagents and solvents were obtained from commercial suppliers and were used without further purification. Melting points (° C.) were determined in open glass capillaries using Electrothermal melting point apparatus (UK) and are uncorrected. Infrared (IR) spectra were recorded on SHIMADZU FT/IR S1 Plus spectrometer (Germany) using potassium bromide (KBr) discs and expressed in wave number υ (cm$^{-1}$). NMR spectra were obtained on an Agilent Technologies 600 Ultra Shield NMR spectrometer (Santa Clara, USA) at 600 MHz for $^1$H and 154 MHz for $^{13}$C. The chemical shifts are expressed in δ (ppm) with reference to tetramethylsilane (TMS). Coupling constants (J) are expressed in Hz. Deuteriochloroform (CDCl$_3$)

and deuteriodimethylsulphoxide (DMSO-$d_6$) were used as solvents. The splitting patterns were designated as: s (singlet), d (doublet), t (triplet), q (quartet), m (multiplet) and br. s (broad singlet). The NMR spectra of compounds 5a, 7a, 8d, 12c, 12d and 12f were obtained on a Bruker Ascend 700 NMR spectrometer (Fallanden, Switzerland) at 700.17 MHz for $^1$H and 176.08 MHz for $^{13}$C. Electron impact mass spectra (EI-MS) were recorded on a Shimadzu GC-MS-QP 2010 instrument (Germany) at 70 eV. Microwave reaction was conducted using a Biotage microwave reactor (Biotage® Initiator+, EXP EU, 400 W, 2450 MHz). Thin layer chromatography (TLC) was performed for monitoring the reactions and checking the purity of the final products using silica gel precoated aluminum sheets (60 F254, Merck) and visualization with Ultraviolet light (UV) at 365 and 254 nm.

Example 2

Synthesis of 4-hydroxy-6-methylcoumarin 4b

Compound 4b was synthesized according to the reported procedure (Shah et al., above). (75.67%, M.P. 259-261° C.). EI-MS, m/z (Rel. Int. %): 176 (M$^+$, 40.7), 147 (100).

Example 3

Synthesis of 2-amino-9-methyl-5-oxo-4-aryl-4H, 5H-pyrano[3,2-c]chromene-3-carbonitriles Compounds 5a, 5b Compounds 5a, 5b were synthesized according to the reported procedure (Kiyani et al., "Efficient tandem synthesis of a variety of pyran-annulated heterocycles, 3,4-disubstituted isoxazol-5(4H)-ones, and α,β-unsaturated nitriles catalyzed by potassium hydrogen phthalate in water" *Res Chem Intermed* 41, 7847-7882, 2015).

(±)-2-amino-9-methyl-4-(4-nitrophenyl)-5-oxo-4H,5H-pyrano[3,2-c]chromene-3-carbonitrile 5a: Yield: 98%. M.P.: 259-61° C. $^1$H NMR (DMSO-$d_6$): δ 2.39 (s, 3H, Ar—CH$_3$), 4.6 (s, 1H, H4), 7.3 (d, J=8.4, 1H, Ar—H), 7.52-7.55 (m, 5H, Ar—H and NH$_2$), 7.67 (s, 1H, Ar—H), 8.1 (d, J=9, 2H, Ar—H). $^{13}$C NMR: δ 20.9 (CH$_3$), 37.23 (C-4), 57.1 (C-3), 103.1 (C-4'a), 119.34 (CN), 112.9, 116.87, 122.58, 124.18, 124.83, 129.58, 131.87, 134.43, 147.01, 151.27 (Ar—C), 154.32 (C-4'b), 158.48 (C=O), 160.11 (C-2). FT/IR (KBr, cm$^{-1}$): υ 2 bands at 3460 and 3346 (NH$_2$), 2204 (CN), 1716 (C=O). EI-MS, m/z (Rel. Int. %): 377 (M+2, 0.13), 73 (100).

(±)-2-amino-4-(furan-2-yl)-9-methyl-5-oxo-4H,5H-pyrano[3,2-c]chromene-3-carbonitrile 5b: Yield: 93.7%. M.P.: 251-3° C. $^1$H NMR (DMSO-$d_6$): δ 2.38 (s, 3H, Ar—CH$_3$), 4.57 (s, 1H, H4), 6.2 (d, J=2.4, 1H, Ar—H), 6.3 (d, J=3.2, 1H, Ar—H), 7.3 (d, J=8.4, 1H, Ar—H), 7.44 (s, 2H, NH$_2$), 7.49 (m, 2H, Ar—H), 7.64 (s, 1H, Ar—H). $^{13}$C NMR: δ 20.95 (CH$_3$), 37.3 (C-4), 55.6 (C-3), 102.32 (C-4'a), 119.1 (CN), 106.8, 110.6, 113.03, 116.82, 122.38, 133.82, 134.43, 142.84, 150.81, 152.93 (Ar—C), 153.94 (C-4'b), 158.72 (C=O), 160.36 (C-2). FT/IR (KBr, cm$^{-1}$): υ 2 bands at 3392 and 3323 (NH$_2$), 2198 (CN), 1701 (C=O). EI-MS, m/z (Rel. Int. %): 321 (M+1, 0.15), 256 (100).

Example 4

2-amino-9-methyl-5-oxo-4-aryl-4H,5H-pyrano[3,2-c]chromene-3-carboxamides Compounds 6a, 6b A mixture of 5a (for compound 6a) or 5b (for compound 6b) (0.01 mol) and conc. H$_2$SO$_4$ (15 ml) was stirred at room temperature for 10-14 hr and then poured on cold water. The formed solid product was collected by filtration, washed with distilled water, dried and crystallized with proper solvent.

(±)-2-amino-9-methyl-4-(4-nitrophenyl)-5-oxo-4H, 5H-pyrano[3,2-c]chromene-3-carboxamide 6a: Cryst. Solvent: EtOH/CHCl$_3$. Yield: 92.9%. M.P.: 142-4° C. 1H NMR (DMSO-$d_6$): δ 2.34 (s, 3H, CH$_3$), 4.86 (s, 1H, H-4), 7.062 (s, 2H, NH$_2$), 7.17 (d, J=9, 2H, Ar—H), 7.38 (d, J=8.4, 1H, Ar—H), 7.53 (s, 2H, NH$_2$), 7.66 (d, J=7.2, 1H, Ar—H), 7.77 (s, 1H, Ar—H), 8.1 (d, J=7.8, 2H, Ar—H). $^{13}$C NMR: 20.93 (CH$_3$), 40.45 (C-4) 54.17 (C-3), 103.47 (C-4'a), 113.04 116.29, 123.32, 124.67, 129.08, 129.78, 133.29, 146.23, 150.19, 150.75 (Ar—C), 151.5 (C-4'b), 160.61 (C=O), 162.44 (C-2), 169.95 (C=O amide). FT/IR (KBr, cm$^{-1}$): υ 2 bands at 3446 and 3408 (NH$_2$), 1734 (C=O ester), 1676 (C=O amide). EI-MS, m/z (Rel. Int. %): 393 (M$^+$, 1.1), 204 (100).

(±)-2-amino-4-(furan-2-yl)-9-methyl-5-oxo-4H,5H-pyrano[3,2-c]chromene-3-carboxamide 6b: Cryst. Solvent: EtOH. Yield: 62.5%. M.P.: 202-4° C. $^1$H NMR (DMSO-$d_6$): δ 2.22 (s, 3H, CH$_3$), 4.83 (s, 1H, H-4), 6.49 (d, J=2.4, 1H, Ar—H), 6.78 (d, J=3.2, 1H, Ar—H), 7.04-7.51 (m, 7H, Ar—H and NH$_2$), 7.79 (s, 1H, Ar—H). $^{13}$C NMR: 20.73 (CH3), 38.68 (C-4), 59.46 (C-3), 103.15 (C-4'a), 109.05, 115.63, 116.55, 121.50, 123.09, 123.45, 133.12, 134.17, 143.68, 151.77 (Ar—C), 152.78 (C-4'b), 162.74 (C=O ester), 163.53 (C-2), 166.56 (C=O amide). FT/IR (KBr, cm$^{-1}$): υ 2 bands at 3446 and 3425 (NH$_2$), 1724 (C=O ester), 1685 (C=O amide). EI-MS, m/z (Rel. Int. %): 339 (M+1, 0.1), 338 (M$^+$, 0.1), 296 (25.82), 73 (100).

Example 5

Synthesis of N'-(3-cyano-9-methyl-5-oxo-4-aryl-4H, 5H-pyrano[3,2-c]chromen-2-yl)-N,N-dimethyl Formimidamides Compounds 7a, 7b A mixture of compound 5a (for compound 7a) or 5b (for compound 7b) (2.7 mmol) and DMF-DMA (25 ml) was heated at 100° C. for 15-40 minutes. Then the solid was filtered, washed with EtOH, dried and crystallized with CHCl$_3$/EtOH.

(±)-N'-(3-cyano-9-methyl-4-(4-nitrophenyl)-5-oxo-4H, 5H-pyrano[3,2-c]chromen-2-yl)-N,N-dimethylformimidamide 7a: Yield: 66.3%. M.P.: 279-81° C. $^1$H NMR (DMSO-$d_6$): δ 2.48 (s, 3H, Ar—CH$_3$), 3.06 (s, 3H, N—CH$_3$), 3.28 (s, 3H, N—CH$_3$), 4.79 (s, 1H, H-4), 7.37 (d, J=8.4, 1H, Ar—H), 7.55 (dd, J=1.4 and J=8.4, 1H, Ar—H), 7.61 (dd, J=2.1 and J=7, 2H, Ar—H), 7.97 (d, J=1.4, 1H, Ar—H), 8.20 (dd, J=2.1 Hz and J=7 Hz, 2H, Ar—H), 8.59 (s, 1H, N=CH). $^{13}$C NMR: 20.85 (Ar—CH$_3$), 34.96 (N—CH$_3$), 41.25 (N—CH$_3$), 38.73 (C-4), 73.05 (C-3), 102.62 (C-4'a), 119.27 (CN), 113.31, 116.79, 123.30, 124.22, 129.88, 134.52, 134.82, 147.16, 150.70, 150.97 (Ar—C), 154.93 (C-4'b), 155.34 (C=N), 157.98 (C=O), 160.32 (C-2). FT/IR (KBr, cm$^{-1}$): a 2204 (CN), 1722 (C=O), 1664 (C=N). EI-MS, m/z (Rel. Int.): 431 (M+1, 0.1), 430 (M$^+$, 0.14), 415 (5.77), 73 (100).

(±)-N'-(3-cyano-4-(furan-2-yl)-9-methyl-5-oxo-4H,5H-pyrano[3,2-c]chromen-2-yl)-N,N-dimethylformimidamide 7b: Yield: 39%. M.P.: 273-5° C. $^1$H NMR (CDCL$_3$): δ 2.43 (s, 3H, Ar—CH$_3$), 3.16 (s, 3H, N—CH$_3$), 3.2 (s, 3H, N—CH$_3$), 4.85 (s, 1H, H-4), 6.31-6.36 (m, 2H, Ar—H), 7.23-7.26 (m, 2H, Ar—H), 7.37 (d, J=8.4, 1H, Ar—H), 7.54 (s, 1H, Ar—H), 8.22 (s, 1H, N=CH). $^{13}$C NMR: 21.04 (Ar—CH$_3$), 35.08 (N—CH$_3$), 41.24 (N—CH$_3$), 32.62 (C-4), 72.96 (C-3), 101.49 (C-4'a), 118.75 (CN), 107.65, 110.8, 113.42, 116.82, 121.8, 133.64, 134.10, 142.25, 150.96, 152.75 (Ar—C), 153.58 (C-4'b), 154.86 (C=N), 159.1 (C=O), 160.55 (C-2). FT/IR (KBr, cm$^{-1}$): υ 2198 (CN), 1724 (C=O), 1654 (C=N). EI-MS, m/z (Rel. Int.): 376 (M+1, 1.9), 99 (100).

Example 6

2-(Arylideneamino)-9-methyl-4-(4-nitrophenyl)-5-oxo-4H, 5H-pyrano[3,2-c]chromene-3-carbonitriles Compounds 8a-8f Aromatic aldehyde (Benzaldehyde [for compounds 8a, 8b], 2,3,4-trimethoxybenzaldehyde [for compounds 8c, 8d] or 2,4-dichlorobenzaldehyde [for compounds 8e, 8f], 1 mmol) was added to a mixture of 5a (for compounds 8a, 8c, 8e) or 5b (for compounds 8b, 8d, 8f)(1 mmol) in 1,4-dioxane and irradiated in microwave (Biotage® Initiator+) for 90-110 min (TLC monitoring). The solvent was evaporated and the residue was washed with toluene to give pure product and dried.

(±)-2-(benzylideneamino)-9-methyl-4-(4-nitrophenyl)-5-oxo-4H,5H-pyrano[3,2-c]chromene-3-carbonitrile 8a: Yield: 23.5%. M.P.: 208-9° C. $^1$H NMR (DMSO-d$_6$): 2.39 (s, 3H, CH$_3$), 4.65 (s, 1H, CH-4), 7.23-7.7 (m, 9H, Ar—H), 8.15-8.39 (m, 4H, Ar—H and N=CH). $^{13}$C NMR: 20.92 (CH$_3$), 37.24 (C-4), 57.19 (C-3), 119.36 (CN), 103.11 (C-4'a), 112.95, 116.85, 122.64, 124.22, 128.03, 128.68, 129.0, 129.35, 129.56, 134.23, 134.49, 134.66, 147.05, 150.90 (Ar—C), 151.30 (C-4'b), 158.48 (C=O), 160.19 (HC=N and C-2). FT/IR (KBr, cm$^{-1}$): υ 2198 (CN), 1701 (C=O), 1670 (C=N). EI-MS, m/z (Rel. Int. %): 465 (M+2, 3.7), 57 (100).

(±)-2-(benzylideneamino)-4-(furan-2-yl)-9-methyl-5-oxo-4H,5H-pyrano[3,2-c]chromene-3-carbonitrile 8b: Yield: 5.8%. M.P.: 250-2° C. $^1$H NMR (DMSO-d$_6$): 2.4 (s, 3H, CH$_3$), 4.42 (s, 1H, CH-4), 7.23-7.50 (m, 11H, Ar—H), 7.70 (s, 1H, HC=N). $^{13}$C NMR: 20.93 (CH$_3$), 37.39 (C-4), 58.41 (C-3), 119.70 (CN), 104.32 (C-4'a), 107.78, 110.51, 113.04, 116.82, 122.54, 127.61, 128.01, 128.66, 129.0, 129.35, 134.27, 134.59, 143.83, 153.85 (Ar—C), 150.77 (C-4'b), 158.45 (C=O), 160.15 (HC=N and C-2). FT/IR (KBr, cm$^{-1}$): υ 2194 (CN), 1703 (C=O), 1670 (C=N). EI-MS, m/z (Rel. Int. %): 410 (M+2, 4), 409 (M+1, 3), 408 (M+, 18), 56 (100).

(±)-9-methyl-4-(4-nitrophenyl)-5-oxo-2-((3,4,5-trimethoxybenzylidene)amino)-4H,5H-pyrano[3,2-c]chromene-3-carbonitrile 8c: Yield: 30.5%. M.P.: 221-3° C. $^1$H NMR (DMSO-d$_6$): 2.37 (s, 3H, CH$_3$), 3.65 (s, 3H, OCH$_3$), 3.94 (s, 6H, OCH$_3$), 4.61 (s, 1H, H-4), 6.47 (s, 2H, Ar—H), 7.23-7.74 (m, 5H, Ar—H), 8.08-8.12 (m, 2H, Ar—H), 9.83 (s, 1H, HC=N). $^{13}$C NMR: 20.82 (CH$_3$), 37.2 (C-4), 56.29 (2 OCH$_3$), 57.21 (C-3), 60.76 (OCH$_3$), 102.9 (C-4'a), 119.45 (CN), 107.11, 112.87, 116.81, 122.71, 123.84, 124.23, 129.50, 131.11, 134.68, 136.86, 139.53, 147.04, 153.23 (Ar—C), 151.20 (C-4'b), 158.54 (C=O), 160.44 (C=N), 160.51 (C-2). FT/IR (KBr, cm$^{-1}$): υ 2200 (CN), 1702 (C=O), 1672 (C=N). EI-MS, m/z (Rel. Int. %): 555 (M+2, 0.1), 554 (M+1, 0.23), 204 (100).

(±)-4-(furan-2-yl)-9-methyl-5-oxo-2-((3,4,5-trimethoxybenzylidene)amino)-4H,5H-pyrano[3,2-c]chromene-3-carbonitrile 8d: Yield: 17.5%. M.P.: 248-50° C. $^1$H NMR (DMSO-d$_6$): δ 2.40 (s, 3H, CH$_3$), 3.36 (s, 3H, OCH$_3$), 3.62-3.7 (m, 6H, OCH$_3$), 4.41 (s, 1H, H-4), 6.42-6.49 (m, 4H, Ar—H), 7.28-7.70 (m, 4H, Ar—H), 9.41 (s, 1H, HC=N). $^{13}$C NMR: 20.93 (CH$_3$), 37.63 (C-4), 56.33 (OCH$_3$+OCH$_3$), 58.3 (C-3), 60.38 (OCH$_3$), 104.0 (C-4'a), 119.74 (CN), 105.29, 113.15, 116.82, 122.61, 134.18, 134.49, 137.02, 139.53, 150.78, 153.27 (Ar—C), 153.93 (C-4'b), 158.47 (C=O), 160.21 (C=N), 160.3 (C-2). FT/IR (KBr, cm$^{-1}$): υ 2196 (CN), 1701 (C=O), 1664 (C=N). EI-MS, m/z (Rel. Int. %): 496 (M−2, 1.18), 135 (100).

(±)-2-((2,4-dichlorobenzylidene)amino)-9-methyl-4-(4-nitrophenyl)-5-oxo-4H,5H-pyrano[3,2-c]chromene-3-carbonitrile 8e: Yield: 37.2%. M.P.: 236-8° C. $^1$H NMR (DMSO-d$_6$): δ 2.42 (s, 3H, CH$_3$), 4.65 (s, 1H, H-4), 7.03-8.4 (m, 10H, Ar—H), 10.27 (s, 1H, HC=N). $^{13}$C NMR: 20.96 (CH$_3$), 37.25 (C-4), 57.16 (C-3), 103.15 (C-4'a), 119.35 (CN), 113.02, 116.91, 122.62, 123.75, 124.21, 128.67, 129.1, 129.6, 129.76, 130.77, 131.11, 131.91, 134.46, 134.6, 147.05, 150.94 (Ar—C), 151.3 (C-4'b), 158.52 (C=O), 160.14 (C-2 and C=N). FT/IR (KBr, cm$^{-1}$): υ 2198 (CN), 1718 (C=O), 1676 (C=N). EI-MS, m/z (Rel. Int. %): 533 (M+1, 0.2), 532 (M$^+$, 3.7), 531 (M−1, 8.7), 530 (M−2, 27.8), 291 (100).

(±)-2-((2,4-dichlorobenzylidene)amino)-4-(furan-2-yl)-9-methyl-5-oxo-4H,5H-pyrano[3,2-c]chromene-3-carbonitrile 8f: Yield: 17.8%. M.P.: >300° C. $^1$H NMR (DMSO-d$_6$): δ 2.38 (s, 3H, CH$_3$), 4.41 (s, 1H, H-4), 7.2-8.1 (m, 9H, Ar—H), 10.11 (s, 1H, HC=N). $^{13}$C NMR: 20.89 (CH$_3$), 37.41 (C-4), 58.52 (C-3), 100.16 (C-4'a), 119.76 (CN), 107.2, 113.53, 116.68, 117.17, 122.21, 122.83, 125.63, 126.2, 128.68, 129.35, 130.92, 131.74, 133.73, 134.38, 148.27, 149.58 (Ar—C) 152.2 (C-4'b), 158.91 (C=O) 160.37 (C-2 and C=N). FT/IR (KBr, cm): υ 2220 (CN), 1718 (C=O), 1647 (C=N). EI-MS, m/z (Rel. Int. %): 478 (M+1, 1.12), 476 (M−1, 2.72), 475 (M−2, 6), 474 (M−3, 8), 91 (100), 73 (100).

Example 7

6-substituted-4-hydroxyl-2-oxo-2H-chromene-3-sulfonyl chloride Compounds 9a, 9b

To a solution of 4a (for compound 9a) or 4b (for compound 9b) (11.3 mmol) in dichloromethane (22.7 ml) cooled to 0° C., chlorosulfonic acid was added (13.5 mmol) dropwise. The reaction mixture was stirred overnight at room temperature. The precipitates were filtered and washed with dichloromethane and petroleum ether, then dried.

6-chloro-4-hydroxy-2-oxo-2H-chromene-3-sulfonyl chloride 9a: Yield: 97%. M.P.: 118-20° C. $^1$H NMR (DMSO-d$_6$): δ 7.39-7.69 (m, 2H, Ar—H), 7.78 (s, 1H, Ar—H), 14.01 (br. s, 1H, OH). $^{13}$C NMR: 108.54 (C-3), 116.76, 118.92, 123.82, 128.61, 133.70, 151.67 (Ar—C), 156.99 (C=O), 161.69 (C-4). FT/IR (KBr, cm$^{-1}$): υ 3317 (br., OH), 1685 (C=O), 1375 (Asymmetric, S—O), 1176 (Symmetric, S—O). EI-MS, m/z (Rel. Int. %): 299 (M+4, 0.2), 298 (M+3, 0.4), 297 (M+2, 2.1), 296 (M+1, 3.5), 295 (M+, 13.21), 294 (M−1, 0.5), 293 (M−2, 0.1), 207 (100).

4-hydroxy-6-methyl-2-oxo-2H-chromene-3-sulfonyl chloride 9b: Yield: 98%. M.P.: 116-7° C. $^1$H NMR (DMSO-d$_6$): δ 2.34 (s, 3H, CH$_3$), 7.21 (d, J=7.8, 1H, Ar—H-7), 7.45 (d, J=8.4, 1H, Ar—H-8), 7.62 (s, 1H, Ar—H-5), 13.96 (br. s, 1H, OH). $^{13}$C NMR: 20.75 (CH$_3$), 107.93 (C-3), 114.90, 116.47, 124.25, 133.95, 134.89, 151.15 (Ar—C), 157.55 (C=O), 162.73 (C-4). FT/IR (KBr, cm$^{-1}$): υ 3381 (br., OH), 1695 (C=O), 1328 (Asymmetric, S—O), 1131 (Symmetric, S—O). EI-MS, m/z (Rel. Int. %): 278 (M+4, 0.07), 277 (M+3, 0.52), 276 (M+2, 2.72), 275 (M+1, 0.23), 274 (M$^+$, 0.05), 44 (100).

Example 8

4-hydroxy-6-(substituted) coumarin-3-sulfonamides Compounds 10a-f

A mixture of 9a (for compounds 10a, 10c, 10e) or 9b (for compounds 10b, 10d, 10f) (0.002 mole), sulfa-compounds (sulfanilamide [for compounds 10a, 10b], sulfadiazine [for compounds 10c, 10d], or sulfathiazole [for compounds 10e, 10f], 0.002 mole), and absolute EtOH (15 ml) was heated under reflux for 3-6 hr (TLC monitoring). The reaction mixture was cooled and the solid was filtered out and washed with Abs. EtOH and petroleum ether, then dried to obtain the pure products.

6-Chloro-4-hydroxy-2-oxo-N-(4-sulfamoylphenyl)-2H-chromene-3-sulfonamide 10a: Yield: 27%. M.P.: 245-7° C. $^1$H NMR (DMSO-d$_6$): δ 5.62 (br. s, 2H, NH$_2$), 6.91-7.04 (m, 3H, Ar—H-2' and 6' and NH), 7.42 (s, 1H, Ar—H), 7.61-7.81 (m, 4H, Ar—H). $^{13}$C NMR: 108.59 (C-3), 116.82, 118.95, 119.04, 122.86, 123.85, 127.86, 128.63, 132.88, 133.70, 151.70 (Ar—C), 157.01 (C=O), 161.69 (C-4). FT/IR (KBr, cm$^{-1}$): υ 3346-3257 (NH$_2$), 3101 (br, OH), 1726 (C=O), 1338 (Asymmetric S—O), 1165 (Symmetric S—O). EI-MS, m/z (Rel. Int. %): 433 (M+3, 0.1), 432(M+2, 0.22), 431 (M+1, 0.85), 430 (M$^+$, 1.9), 73 (100).

4-Hydroxy-6-methyl-2-oxo-N-(4-sulfamoylphenyl)-2H-chromene-3-sulfonamide 10b: Yield: 56%. M.P.: 241-3° C. $^1$H NMR (DMSO-d$_6$): δ 2.36 (s, 3H, CH$_3$), 2.49 (s, 1H, NH), 4.55 (br. s, 2H, NH$_2$), 6.98 (d, J=8.4, 2H, Ar—H-2' and 6'), 7.24 (d, J=8.4, 1H, Ar—H-7), 7.471 (d, J=7.8, 1H, Ar—H-8), 7.65 (m, 3H, Ar—H-8, 3' and 5'), 13.97 (br. s, 1H, OH). $^{13}$C NMR: 20.78 (CH$_3$), 107.98 (C-3), 114.9, 116.51, 117.84, 124.28, 127.85, 133.99, 134.93, 151.17 (Ar—C), 157.65 (C=O), 162.79 (C-4). FT/IR (KBr, cm$^{-1}$): υ 3352 and 3250 (NH$_2$), 3142 (br.), OH), 1680 (C=O), 1355 (Asymmetric S—O), 1157 (Symmetric S—O). EI-MS, m/z (Rel. Int. %): 411 (M+1, 0.51), 410 (M$^+$, 2.62), 408 (M−2, 12.76), 133 (100).

6-Chloro-4-hydroxy-2-oxo-N-(4-(N-(pyrimidin-2-yl)sulfamoyl)phenyl)-2H-chromene-3-sulfonamide 10c: Yield: 78.2%. M.P.: 230-2° C. $^1$H NMR (DMSO-d$_6$): δ 4.71 (br. s, 1H, NH), 6.65 (d, J=9.6, 2H, Ar—H-2' and 6'), 7.01 (m, 1H, Diazine-H-4), 7.41-7.72 (m, 5H, Ar—H and NH), 7.81 (s, 1H, Ar—H-5), 8.47 (m, 2H, Diazine-H-3 and 5). $^{13}$C NMR: 108.61 (C-3), 113.78, 116.00, 116.83, 118.94, 123.85, 126.84, 128.61, 130.23, 133.69, 151.72, 156.97, 158.73 (Ar—C), 157.61 (C=O), 161.66 (C-4). FT/IR (KBr, cm$^{-1}$): υ 3373 (NH), 3084 (br, OH), 1691 (C=O), 1346 (Asymmetric S—O), 1151 (Symmetric S—O). EI-MS, m/z (Rel. Int. %): 511 (M+3, 0.6), 315 (100).

4-hydroxy-6-methyl-2-oxo-N-(4-(N-(pyrimidin-2-yl)sulfamoyl)phenyl)-2H-chromene-3-sulfonamide 10d: Yield: 86.3%. M.P.: 207-9° C. $^1$H NMR (DMSO-d$_6$): δ 2.39 (s, 3H, CH$_3$), 6.63 (d, J=9.6, 2H, Ar—H-2' and 6'), 7.02 (m, 1H, Diazine-H-4), 7.27 (d, J=10.8, 1H, Ar—H-8), 7.49 (d, J=9.6, 1H, Ar—H-7), 7.64-7.67 (m, 3H, Ar—H-5, 3' and 5'), 8.49 (m, 2H, Diazine-H-3 and 5). $^{13}$C NMR: 20.78 (CH$_3$), 108.00 (C-3), 113.31, 114.95, 116.00, 116.5, 124.29, 126.23, 128.27, 128.44, 130.25, 133.95, 134.88, 151.19, 158.72 (Ar—C), 157.62 (C=O), 162.73 (C-4). FT/IR (KBr, cm$^{-1}$): υ 3620.39 (OH), 3423 and 3356 (2NH), 1691 (C=O), 1334 (Asymmetric S—O), 1166 (Symmetric S—O). EI-MS, m/z (Rel. Int. %): 490 (M+2, 2.54), 489 (M+1, 5.08), 355 (100).

6-chloro-4-hydroxy-2-oxo-N-(4-(N-(thiazol-2-yl)sulfamoyl)phenyl)-2H-chromene-3-sulfonamide 10e: Yield: 74.13%. M.P.: 215-7° C. $^1$H NMR (DMSO-d$_6$): δ 5.35 (br. s, 1H, NH), 5.4 (br. s, 1H, NH), 6.78 (d, J=3.6, 1H, Thiazole-H), 6.86 (d, J=8.4, 2H, Ar—H-2' and 6'), 7.22 (d, J=3.6, 1H, Thiazole-H), 7.42 (d, J=8.4, 1H, Ar—H-8), 7.58 (d, J=9.6, 2H, Ar—H-3' and 5'), 7.72 (d, J=7.8, 1H, Ar—H-7), 7.81 (s, 1H, Ar—H-5). $^{13}$C NMR: 108.60 (C-3), 108.30, 116.64, 116.82, 118.95, 123.85, 124.87, 128.13, 128.63, 132.85, 133.70, 147.15, 151.71, 168.78 (Ar—C), 157.01 (C=O), 161.69, (C-4). FT/IR (KBr, cm$^{-1}$): υ 3448 (NH), 3140 (br., OH), 1676 (C=O), 1338 (Asymmetric S—O), 1147 (Symmetric S—O). EI-MS, m/z (Rel. Int. %): 514 (M+1, 0.2), 513 (M$^+$, 1.2), 73 (100).

4-hydroxy-6-methyl-2-oxo-N-(4-(N-(thiazol-2-yl)sulfamoyl)phenyl)-2H-chromene-3-sulfonamide 10f: Yield: 84.7%. M.P.: 167-9° C. $^1$H NMR (DMSO-d$_6$): δ 2.37 (s, 3H, CH$_3$), 6.74 (m, 3H, Ar—H-2' and 6' and thiazole-H), 7.19 (d, J=3.6, 1H, Thiazole-H), 7.24 (d, J=8.4, 1H, Ar—H-8), 7.47 (d, J=7.8, 1H, Ar—H-7), 7.51 (d, J=8.4, 2H, Ar—H-3' and 5'), 7.65 (s, 1H, Ar—H-5), 13.99 (br. s, 1H, OH). $^{13}$C NMR: 20.78 (CH$_3$), 107.97 (C-3), 108.18, 114.94, 115.34, 116.50, 124.28, 124.80, 128.15, 131.25, 133.96, 134.90, 145.99, 151.18, 168.66 (Ar—C) 157.57 (C=O), 162.74 (C-4). FT/IR (KBr, cm$^{-1}$): υ 3421(OH) overlapped with 3338 (NH), 1683 (C=O), 1350 (Asymmetric S—O), 1153 (Symmetric S—O). EI-MS, m/z (Rel. Int. %): 493 (M$^+$, 0.1), 491(M−2, 3.2), 490 (M−3, 3.2), 73 (100).

Example 9

4-hydroxy-6-(substituted)coumarin-3-sulfonamides Compounds 11a-11f

A mixture of 9a (for compounds 11a, 11c, 11e) or 9b (for compounds 11b, 11d, 11f) (0.002 mole), 4-substituted-aniline (aniline (for compounds 11a, 11b), 4-hydroxyaniline (for compounds 11c, 11d) or 4-acetylaniline (for compounds 11e, 11f), 0.004 mole) and absolute EtOH (15 ml) was heated under reflux for 6-8 hr. While warm, the solid was filtered out, washed with hot absolute ethanol then petroleum ether, dried and recrystallized, if necessary.

6-Chloro-4-hydroxy-2-oxo-N-phenyl-2H-chromene-3-sulfonamide 11a: Yield: 92.65%. M.P.: 337-9° C. $^1$H NMR (DMSO-d$_6$): δ 7.27-7.46 (m, 6H, Ar—H), 7.72 (d, J=8.4, 1H, Ar—H), 7.80 (s, 1H, Ar—H-5). $^{13}$C NMR: 108.61 (C-3), 116.82, 117.67, 118.96, 122.73, 123.86, 127.55, 128.63, 130.25, 133.72, 151.72 (Ar—C), 157.02 (C=O), 161.69 (C-4). FT/IR (KBr, cm$^{-1}$): υ 3367 (sharp NH), 3169 (br., OH), 1683 (C=O), 1348 (Asymmetric S—O), 1168 (Symmetric S—O). EI-MS, m/z (Rel. Int. %): 350 (M−1, 1.18), 57 (100).

4-Hydroxy-6-methyl-2-oxo-N-phenyl-2H-chromene-3-sulfonamide 11b: Yield: 84.5%. M.P.: 324-5° C. $^1$H NMR (DMSO-d$_6$): δ 2.37 (s, 3H, CH$_3$), 7.30-7.65 (m, 8H, Ar—H), 9.65 (br. s, 1H, NH), 13.96 (br. s, 1H, OH). $^{13}$C NMR: 20.79 (CH$_3$), 107.98 (C-3), 114.95, 116.51, 123.06, 124.29, 127.96, 130.26, 133.19, 133.96, 134.90, 151.19 (Ar—C), 157.66 (C=O), 162.77 (C-4). FT/IR (KBr, cm$^{-1}$): υ 3356 (NH), 3111 (br., OH), 1685 (C=O), 1354(Asymmetric S—O), 1159 (Symmetric S—O). EI-MS, m/z (Rel. Int. %): 434 (M+3, 1.65), 333(M+2, 3.92), 332 (M+1, 26.25), 207 (100).

6-Chloro-4-hydroxy-N-(4-hydroxyphenyl)-2-oxo-2H-chromene-3-sulfonamide 11e: Cryst. Solvent: CHCl$_3$. Yield: 48.3%. M.P.: 250-1° C. $^1$H NMR (DMSO-d$_6$): δ 6.83 (m, 2H, Ar—H-2' and 6'), 7.12 (m, 2H, Ar—H-3' and 5'), 7.42 (s, J=8.4, 1H, Ar—H-8), 7.73 (d, J=7.8, 1H, Ar—H-7), 7.82 (s, 1H, Ar—H-5), 9.73 (s, 1H, NH), 10.06 (br. s, 1H, OH). $^{13}$C NMR: 108.58 (C-3), 116.56, 116.82, 118.96, 123.87, 124.20, 128.65, 133.74, 151.71, 160.19 (Ar—C), 157.09

(C=O), 161.73 (C-4). FT/IR (KBr, cm$^{-1}$): υ 3278 (br., OH overlapped with NH), 1681 (C=O), 1346 (Asymmetric S—O), 1168 (Symmetric S—O). EI-MS, m/z (Rel. Int. %): 366 (M–1, 0.1), 363 (M–4, 28.19), 332 (5.86), 196 (100).

4-Hydroxy-N-(4-hydroxyphenyl)-6-methyl-2-oxo-2H-chromene-3-sulfonamide 11d: Cryst. Solvent: CHCl$_3$. Yield: 63.13%. M.P.: 253-4° C. $^1$H NMR (DMSO-d$_6$): δ 2.38 (s, 3H, CH$_3$), 6.82 (m, 2H, Ar—H-2' and 6'), 7.12-7.25 (m, 3H, Ar—H-3', 5' and 8), 7.49-7.65 (m, 2H, Ar—H-7 and 5), 9.75 (br. s, 1H, NH). $^{13}$C NMR: 20.79 (CH$_3$), 107.98 (C-3), 114.95, 116.56, 123.49, 124.28, 124.38, 133.96, 134.90, 151.19, 157.27, 173.79 (Ar—C), 157.61 (C=O), 162.75 (C-4). FT/IR (KBr, cm$^{-1}$): υ 3298 (br., OH overlapped with NH), 1662 (C=O), 1354 (Asymmetric S—O), 1166 (Symmetric S—O). EI-MS, m/z (Rel. Int. %): 345 (M–2, 0.04), 344 (M–3, 0.48), 343 (M–4, 3.31), 342 (M–5, 9.7), 341 (M–6, 52.35), 209 (100).

N-(4-acetylphenyl)-6-chloro-4-hydroxy-2-oxo-2H-chromene-3-sulfonamide 11e: Cryst. Solvent: CHCl$_3$/isopropanol. Yield: 81.25%. M.P.: 238-40° C. $^1$H NMR (DMSO-d$_6$): δ 2.38 (s, 3H, O=C—CH$_3$), 6.69 (s, 2H, Ar—H-2' and 6'), 7.37 (d, J=7.8, 1H, Ar—H-8), 7.69 (m, 3H, Ar—H-3', 5' and 7), 7.77 (s, 1H, Ar—H-5), 13.97 (br. s, 1H, OH). $^{13}$C NMR: 26.44 (CH$_3$), 108.54 (C-3), 115.01, 116.77, 118.89, 123.81, 127.46, 128.59, 130.86, 133.67, 150.63, 151.66 (Ar—C), 156.95 (C=O ester), 161.66 (C-4), 195.83 (C=O ketone). FT/IR (KBr, cm$^{-1}$): υ 3344 (NH), 3088 (br., OH), 1718 (C=O ketone), 1678 (C=O ester), 1357 (Asymmetric S—O), 1166 (Symmetric S—O). EI-MS, m/z (Rel. Int. %): 397 (M+4, 0.13), 391 (M–2, 0.13), 390 (M–3, 0.83), 54 (100).

N-(4-acetylphenyl)-4-hydroxy-6-methyl-2-oxo-2H-chromene-3-sulfonamide 11f: Cryst. Solvent: CHCl$_3$/isopropanol. Yield: 74.5%. M.P.: 231-2° C. $^1$H NMR (DMSO-d$_6$): δ 2.37 (s, 3H, CH$_3$), 2.38 (s, 3H, O=C—CH$_3$), 6.62 (d, J=7.8, 2H, Ar—H-2' and 6'), 7.24 (d, 1H, J=9, Ar—H-8), 7.47 (d, J=8.4, 1H, Ar—H-7), 7.66-7.69 (m, 3H, Ar—H-5, 3' and 5'), 13.96 (br. s, 1H, OH). $^{13}$C NMR: 20.76 (CH$_3$), 26.64 (CH$_3$—C=O), 107.92 (C-3) 114.90, 116.49, 116.98, 124.27, 129.46, 130.75, 133.96, 134.91, 147.57, 151.15 (Ar—C), 157.63 (C=O ester), 162.77 (C-4), 196.18 (C=O ketone). FT/IR (KBr, cm$^{-1}$): υ 3342 (NH), 3068 (br., OH), 1728 (C=O ketone), 1707 (C=O ester), 1359 (Asymmetric S—O), 1163 (Symmetric S—O). EI-MS, m/z (Rel. Int. %): 377 (M+4, 0.1), 476 (M+3, 0.5), 375 (M+2, 2.4), 374 (M+1, 4), 373 (M$^+$, 15.3), 73 (100).

Example 10

Coumarin-Sulfonamide Chalcones Compounds 12a-f

Equimolar quantities of 11e (for compounds 12a, 12c, 12e) or 11f (for compounds 12b, 12d, 12f) (0.01 mole) and aromatic aldehyde (4-nitrobenzaldehyde [for compounds 12a, 12b], 4-chlorobenzaldehyde [for compounds 12c, 12d] or 4-methoxybenzaldehyde [for compounds 12e, 12f]) 0.01 mole) were dissolved in minimum amount of ethanol. Sodium hydroxide solution (2 ml, 0.02 M) was added slowly and stirred for 24 hr, at room temperature. The mixture was poured slowly into 400 ml of ice water with constant stirring and kept in a refrigerator for 24 hr. The precipitate obtained was filtered, washed with distilled water, dried and recrystallized, if necessary with CHCl$_3$.

(E)-6-chloro-4-hydroxy-N-(4-(3-(4-nitrophenyl)acryloyl)phenyl)-2-oxo-2H-chromene-3-sulfonamide 12a: Yield: 35.34%. M.P.: 205-7° C. $^1$H NMR (DMSO-d$_6$): δ 6.30-6.66 (m, 4H, Ar—H), 7.73 (d, J=9, 1H, Ar—H), 7.99-8.3 (m, 9H, CH$_a$=CH$_b$, Ar—H and NH). $^{13}$C NMR: 101.1 (C-3), 122.06 (C=C$_a$), 142.34 (C=C$_b$), 113.28, 115.98, 124.42, 124.60, 125.49, 127.2, 130.00, 130.45, 130.56, 130.83, 131.94, 139.16, 148.22, 151.20 (Ar—C), 157.78 (C=O ester), 161.98 (C-4), 185.92 (C=O ketone). FT/IR (KBr, cm$^{-1}$): υ Sharp 3487 (OH), 3388 (NH), 1703 (C=O ester), 1637 (C=O ketone), 1342 (Asymmetric S—O), 1180 (Symmetric S—O). EI-MS, m/z (Rel. Int. %): 527 (M+1, 8), 526 (M$^+$, 11), 373 (100).

(E)-4-hydroxy-6-methyl-N-(4-(3-(4-nitrophenyl)acryloyl)phenyl)-2-oxo-2H-chromene-3-sulfonamide 12b: Yield: 30%. M.P.: 220-2° C. $^1$H NMR (DMSO-d$_6$): δ 2.38 (s, 3H, CH$_3$), 6.67-6.78 (m, 4H, Ar—H), 7.25 (s, 1H, Ar—H), 7.49-8.34 (m, 9H, CH$_a$=CH$_b$, Ar—H, and NH), 13.98 (br. s, 1H, OH). $^{13}$C NMR: 20.82 (CH$_3$), 107.95 (C-3) 121.67 (C=C$_a$), 141.94 (C=C$_b$), 114.92, 116.41, 116.84, 123.55, 124.37, 128.48, 129.38, 130.75, 133.96, 134.91, 138.21, 140.74, 145.97, 151.15 (Ar—C), 157.65 (C=O ester), 162.32 (C-4), 186.10 (C=O ketone). FT/IR (KBr, cm$^{-1}$): υ Sharp 3487 (OH), 3388 (NH), 1707 (C=O ester), 1637 (C=O ketone), 1340 (Asymmetric S—O), 1182 (Symmetric S—O). EI-MS, m/z (Rel. Int. %): 506 (M$^+$, 0.24), 503 (M–3, 1.61), 73 (100).

(E)-6-chloro-N-(4-(3-(4-chlorophenyl)acryloyl)phenyl)-4-hydroxy-2-oxo-2H-chromene-3-sulfonamide 12c: Yield: 22.32%. M.P.: 157-9° C. $^1$H NMR (DMSO-d$_6$): 5.64 (s, 1H, NH), 6.64 (m, 2H, Ar—H), 7.44 (d, J=8.4, 1H, Ar—H), 7.51 (d, J=8.4, 1H, Ar—H), 7.61 (d, J=16.1, 1H, C=CH$_a$), 7.73 (dd., J=2.5, J=6.3, 2H, Ar—H), 7.83 (d, J=8.4, 1H, Ar—H), 7.89-7.92 (m, 3H, Ar—H and C=CH$_b$), 7.95 (d, J=8.4, 2H, Ar—H), 14.13 (br. s, 1H, OH). $^{13}$C NMR: 108.63 (C-3), 122.85, (C=C$_a$), 140.45 (C=C$_b$), 113.40, 116.84, 118.95, 123.65, 123.86, 128.62, 129.33, 130.69, 131.67, 132.89, 133.70, 134.62, 134.86, 151.72 (Ar—C), 156.97 (C=O ester), 161.67 (C-4), 186.18 (C=O ketone). FT/IR (KBr, cm$^{-1}$): υ Sharp 3460 (OH), 3340 (NH), 1703 (C=O ester), 1629 (C=O ketone), 1346 (Asymmetric S—O), 1176 (Symmetric S—O). EI-MS, m/z (Rel. Int. %): 519 (M+3, 0.3), 518 (M+2, 0.6), 517 (M+1, 1.6), 221 (100).

(E)-N-(4-(3-(4-chlorophenyl)acryloyl)phenyl)-4-hydroxy-6-methyl-2-oxo-2H-chromene-3-sulfonamide 12d: Yield: 22.41%. M.P.: 141-3° C. $^1$H NMR (DMSO-d$_6$): δ 2.39 (s, 3H, CH$_3$), 6.75 (d, J=8.4, 2H, Ar—H), 7.27 (d, J=8.4, 1H, Ar—H), 7.49-7.52 (m, 3H, Ar—H), 7.63 (d, J=15.4, 1H, C=CH$_a$), 7.67 (s, 1H, Ar—H), 7.89-7.92 (m, 3H, Ar—H and C=CH$_b$), 7.99 (d, J=9.1, 2H, Ar—H), 14.09 (s, 1H, OH). $^{13}$C NMR: 20.80 (CH$_3$), 108.03 (C-3), 123.57 (C=C$_a$), 140.79 (C=C$_b$), 114.58, 114.98, 116.51, 124.30, 129.35, 129.86, 130.75, 131.56, 131.67, 133.93, 134.55, 134.87, 134.97, 151.20 (Ar—C), 157.54 (C=O ester), 162.72 (C-4), 186.44 (C=O ketone). FT/IR (KBr, cm$^{-1}$): υ Sharp 3462 (OH), 3342 (NH), 1701 (C=O ester), 1647 (C=O ketone), 1346 (Asymmetric S—O), 1178 (Symmetric S—O). EI-MS, m/z (Rel. Int. %): 497 (M+2, 1.1), 496 (M+1, 10.4), 495 (M$^+$, 60.46), 55 (100).

(E)-6-chloro-4-hydroxy-N-(4-(3-(4-methoxyphenyl)acryloyl)phenyl)-2-oxo-2H-chromene-3-sulfonamide 12e: Yield: 30.23%. M.P.: >300° C. $^1$H NMR (DMSO-d$_6$): δ 3.80 (s, 3H, OCH$_3$), 6.60 (d, J=7.7, 2H, Ar—H), 6.98 (m, 2H, Ar—H), 7.09 (m, 2H, Ar—H), 7.35 (d, J=8.4, 1H, Ar—H), 7.57 (d, J=8.4, 1H, Ar—H), 7.72-7.90 (m, 3H, Ar—H, C=CH$_a$ and C=CH$_b$), 8.20 (d, J=8.4, 2H, Ar—H), 8.59 (s, 1H, NH). $^{13}$C NMR: 55.791 (OCH$_3$), 108.30 (C-3), 120.34 (C=C$_a$), 141.82 (C=C$_b$), 113.16, 114.78, 119.94, 121.67, 125.98, 128.25, 129.10, 130.41, 130.75, 131.29, 131.45, 135.29, 144.14, 161.30 (Ar—C), 157.17 (C=O ester), 162.04 (C-4), 186.34 (C=O ketone). FT/IR (KBr, cm$^{-1}$): υ Sharp 3468 (OH), 3329 (NH), 1695 (C=O ester), 1626 (C=O ketone), 1350 (Asymmetric S—O), 1163 (Symmetric S—O). EI-MS, m/z (Rel. Int. %): 513 (M+2, 0.12), 73 (100).

(E)-4-hydroxy-N-(4-(3-(4-methoxyphenyl)acryloyl)phenyl)-6-methyl-2-oxo-2H-chromene-3-sulfonamide 12f: Yield: 15.2%. M.P.: >300° C. $^1$H NMR (DMSO-d$_6$): 2.39 (s, 3H, CH$_3$), 3.87 (s, 3H, OCH$_3$), 6.83 (d, J=7.7, 2H, Ar—H), 7.01 (d, J=7.7, 2H, Ar—H), 7.27 (d, J=8.4, 1H, Ar—H), 7.50 (d, J=8.4, 1H, Ar—H), 7.64 (d, J=15.4, 1H, C=CH$_a$), 7.67 (s, 1H, Ar—H$_5$), 7.76 (d, J=15.4, 1H, C=CH$_b$), 7.82 (d, J=7.7, 2H, Ar—H), 8.00 (d, J=8.2, 2H, Ar—H), 14.04 (br. s, 1H, OH). $^{13}$C NMR: 20.79 (CH$_3$), 55.81 (OCH$_3$), 108.00 (C-3), 120.19 (C=C$_a$), 142.53 (C=C$_b$), 114.81, 114.98, 115.54, 116.51, 124.30, 128.55, 130.9, 130.89, 131.25, 132.30, 133.96, 134.90, 151.20, 161.45 (Ar—C), 157.60 (C=O ester), 162.76 (C-4), 186.80 (C=O ketone). FT/IR (KBr, cm$^{-1}$): υ Sharp 3468 (OH), 3331 (NH), 1701 (C=O ester), 1626 (C=O ketone), 1342 (Asymmetric S—O), 1163 (Symmetric S—O). EI-MS, m/z (Rel. Int. %): 491 (M$^+$, 0.8), 490 (M−1, 5.29), 78 (100).

Example 11

Testing Properties of Coumarin Derivatives—Overview

In summary, compounds 11c, 11d, 11a and 11b demonstrated particularly high antioxidant activity. Compounds 10a, 10c, 10d, 11a, 11c, 11d, 12c and 12d exhibited antimicrobial activity equal to or higher than the standard antimicrobials (ciprofloxacin and ketoconazole) against one or more microorganisms. In particular, compound 10d showed a broad-spectrum activity against all of the tested microorganisms. Compounds 6a, 5b, 8c, 12a and 6b showed more potent in vitro anti-proteinase activity than aspirin, and compounds 8d, 8e, 10f, 11a and 11c showed as potent anti-proteinase activity as aspirin, with compound 6a showing significant in vivo anti-inflammatory activity. These compounds, except 8c, 10c and 12c, followed the in silico criteria for orally active drug, and therefore they will be studied in vivo to be developed as orally active agents. The potent compounds such as 11c, 10d and 6a may serve as "lead compound" to develop more potent and high-efficiency antioxidant, antimicrobial and/or anti-inflammatory agents.

Example 12

Antioxidant Activity of Coumarin Derivatives

The antioxidant activity of the synthesized compounds was measured in terms of hydrogen-donating or radical scavenging ability using the DPPH microplate-based method. Absorbance measurement was obtained using Microplate/cuvette reader (Spectramax M5, Molecular Devices, California, USA). Reference standard compound ascorbic acid was used as the positive control for this assay at concentrations ranging from 1.563 to 200 µg/mL. Test samples were prepared at a starting concentration of 200 µg/mL after mixing with 100 µl of 0.2 mM DPPH methanolic solution. A series of concentrations were tested for the samples in order to determine the 50% inhibitory concentration (IC$_{50}$). Samples were incubated with DPPH in the dark for 30 min at room temperature (25° C.). The DPPH solution in methanol was prepared daily and stored in a flask covered with aluminum foil. DPPH radicals have an absorption maximum ($\lambda_{max}$) at 515 nm, in which the absorbance values were measured and converted into percentage of antioxidant activity.

Methanolic DPPH solution without antioxidant was applied as control and background control was samples in methanol only. IC$_{50}$ was determined using Graphpad Prism 7 (Graphpad Software Inc. CA, USA). The percentage inhibition was calculated by using the formula:

$$\% \text{ Inhibition} = 100 - \left[ \frac{(\text{Sample Absorbance} - \text{Sample background Absorbance})}{DPPH \text{ only Absorbance}} \times 100 \right]$$

The assay was carried out in triplicate and performed as much as possible in an area protected against light. The data points are presented as the mean±standard deviation (SD) (n=3).

Antioxidant effects of test sample compounds prepared according to the exemplary synthetic methods, as well as ascorbic acid control, were obtained by a 2,2-diphenyl-1-picrylhydrazyl (DPPH) antioxidant assay and are summarized in Tables 3 and 4. Fourteen of the test sample compounds were found to have radical scavenging activity, and dose dependent antioxidant activity was observed for all compounds having antioxidant activity. The redox properties of the test sample compounds may contribute to their antioxidant activity, which allows them to act as hydrogen atom donors or reducing agents and scavenge-free radicals.

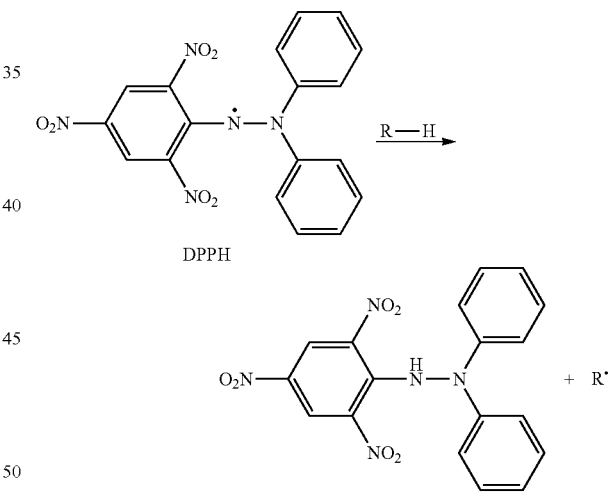

Only compounds 6b and 8d among the pyranocoumarins showed modest antioxidant activity, with the IC$_{50}$ values of 48.38±4.61 and 82.92±3.30 µg/mL, respectively. Similarly, the coumarin-sulfonamide derivatives 10a-f had comparable activities to compounds 6b and 8d, with the IC$_{50}$ values in the range of 61-120 µg/mL. Significant antioxidant activity was observed in compounds 11a-f, with IC$_{50}$ values in the range of 3-35 µg/mL, compounds 11e and 11d being the most potent among this series. The coumarin-sulfonamide chalcones 12a-f demonstrated poorer antioxidant activity, with IC$_{50}$ values >200 µg/mL.

Based on the experimental results, the pyranocoumarins 6b and 8d have good radical scavenging activity, possibly related to the presence of a furyl ring at position 4 of the coumarin base structure. Compound 6b exhibits superior antioxidant activity, possibly due to the presence of an amino group and carboxamide at positions 2 and 3, respectively. However, the remaining pyranocoumarin compounds, synthesized as above, showed relatively poor antioxidant activity.

Of the exemplarily synthesized coumarin-3-sulfonamides, generally, the chloro-substituted compounds at 6-position of the base coumarin ring show higher radical scavenging potential than the analogous methyl-substituted compounds. Interestingly, compounds 11c and 11d exhibit the highest antioxidant activity. The presence of the phenolic hydroxyl group might explain this optimal activity. Compounds 11a, 11b, 11e, and 11f show good radical scavenging potential relative to standard control ascorbic acid. The sulfathiazole containing compounds, 10e and 10f, and sulfanilamide containing compounds, 10a and 10b, show higher antioxidant activity than sulfadiazine substituted compounds, 10c and 10d.

The selected pyranocoumarins tested in Table 3 are as follows:

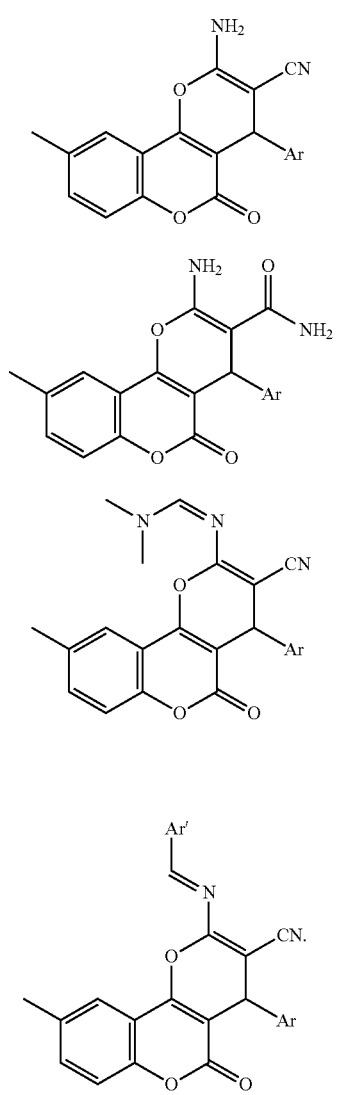

TABLE 3

Antioxidant activity of selected pyranocoumarin derivatives

| Compound no. | Ar | Ar' | $IC_{50}^{a,b}$ (µg/mL) |
|---|---|---|---|
| 5a | 4-NO$_2$C$_6$H$_4$ | — | — |
| 5b | 2-Furyl | — | — |
| 6a | 4-NO$_2$C$_6$H$_4$ | — | — |
| 6b | 2-Furyl | — | 48.38 ± 4.616 |
| 7a | 4-NO$_2$C$_6$H$_4$ | — | — |
| 7b | 2-Furyl | — | — |
| 8a | 4-NO$_2$C$_6$H$_4$ | C$_6$H$_5$ | — |
| 8c | 4-NO$_2$C$_6$H$_4$ | 3,4,5-(OCH$_3$)$_3$C$_6$H$_2$ | — |
| 8d | 2-Furyl | 3,4,5-(OCH$_3$)$_3$C$_6$H$_2$ | 82.92 ± 3.300 |
| 8e | 4-NO$_2$C$_6$H$_4$ | 2,4-diCl C$_6$H$_3$ | — |
| 8f | 2-Furyl | 2,4-diCl C$_6$H$_3$ | — |
| Ascorbic acid * | | | 2.83 ± 0.166 |

$^a$mean ± SD (n = 3).
$^b$(—): inactive (IC$_{50}$ > 200 µg/mL).
* Positive control.

The selected coumarin sulfonamide derivatives tested in Table 4 are as follows:

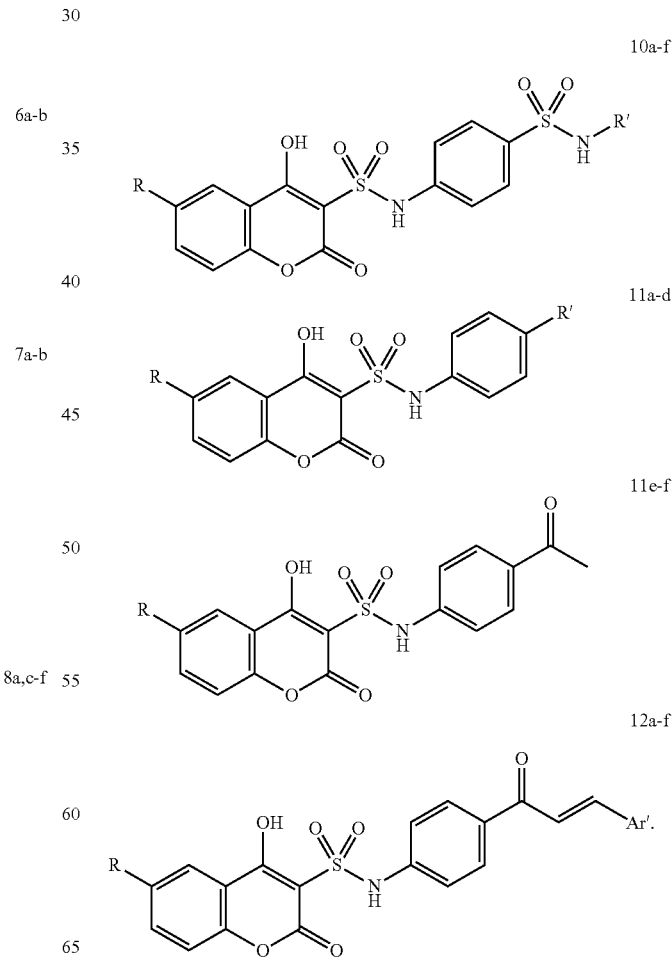

TABLE 4

Antioxidant activity of selected coumarin sulfonamide derivatives

| Compound no. | R | R'/Ar' | $IC_{50}^{a,\,b}$ (μg/mL) |
|---|---|---|---|
| 10a | Cl | H | 93.12 ± 0.727 |
| 10b | CH$_3$ | H | 61.78 ± 2.719 |
| 10c | Cl | pyrimidin-2yl | 120.12 ± 4.629 |
| 10d | CH$_3$ | pyrimidin-2yl | 112.19 ± 4.391 |
| 10e | Cl | thiazol-2-yl | 71.67 ± 3.231 |
| 10f | CH$_3$ | thiazol-2-yl | 83.52 ± 1.849 |
| 11a | Cl | H | 14.51 ± 1.827 |
| 11b | CH$_3$ | H | 19.25 ± 4.171 |
| 11c | Cl | OH | 3.87 ± 0.409 |
| 11d | CH$_3$ | OH | 4.30 ± 0.531 |
| 11e | Cl | — | 32.85 ± 1.322 |
| 11f | CH$_3$ | — | 35.36 ± 3.265 |
| 12a | Cl | 4-NO$_2$C$_6$H$_4$ | — |
| 12b | CH$_3$ | 4-NO$_2$C$_6$H$_4$ | — |
| 12c | Cl | 4-ClO$_6$H$_4$ | — |
| 12d | CH$_3$ | 4-ClO$_6$H$_4$ | — |
| 12e | Cl | 4-MeOC$_6$H$_4$ | — |
| 12f | CH$_3$ | 4-MeOC$_6$H$_4$ | — |
| Ascorbic acid * | | | 2.83 ± 0.166 |

$^a$mean ± SD (n = 3).
$^b$(—): inactive (IC$_{50}$ > 200 μg/mL).
* Positive control.

Example 13

Antimicrobial Activity of Coumarin Derivatives

The newly synthesized compounds were individually tested for their in vitro antimicrobial activity against the standard bacteria strains of American Type Culture Collection (ATCC), namely, *Staphylococcus aureus* ATCC 29213, *Bacillus subtilis* ATCC 6633, *Bacillus megaterium* ATCC 9885 (Gram-positive), *Escherichia coli* ATCC 2592 and *Pseudomonas aeruginosa* ATCC 27953 (Gram-negative). In addition, they were microbiologically tested against the locally isolated *Saccharomyces cerevisiae* (yeast) and the standard strain of Agricultural Research Service Culture Collection (NRRL) of the yeast like pathogenic fungus *Candida albicans* NRRL Y-477. The primary screening was carried out using the agar well diffusion method using nutrient agar (NA) medium and Sabourand dextrose agar (SDA) medium for pathological tested bacteria and yeast, respectively. The minimal inhibitory concentration for the most active compounds (having inhibition zones (IZ) >16 mm) against the same microorganisms used in the primary screening was evaluated using the two fold serial dilution technique using the proper nutrient broth.

Antimicrobial tests were carried out by the agar well diffusion method using 100 μL of suspension containing 1×10$^8$ CFU/mL of pathological tested bacteria and 1×10$^6$ CFU/ml of yeast spread on NA and SDA, respectively. After the media was cooled and solidified, wells (10 mm in diameter) were made in the solidified agar and loaded with 100 μL of tested compound solution prepared by dissolving 10 mg of the chemical compound in one ml of dimethyl sulfoxide (DMSO). The inculcated plates were then incubated for 24 h at 37° C. for bacteria and yeast. Negative controls were prepared using DMSO employed for dissolving the tested compound. Ciprofloxacin (10 mg/ml) and ketoconazole (10 mg/ml) were used as standard for antibacterial and antifungal activity, respectively. After incubation time, antimicrobial activity was evaluated by measuring the zone of inhibition against the test organisms and compared with that of the standard. Antimicrobial activities were expressed as inhibition diameter zones in millimeters (mm). The experiment was carried out in triplicate and the average zone of inhibition was calculated.

The bacteriostatic activity of the active compounds (having IZ>16 mm) was then evaluated using the two fold serial dilution technique. Two-fold serial dilutions of the tested compound solutions were prepared using the proper nutrient broth. The final concentration of the solutions were 1000, 500, 250 and 125 μg/ml. The tubes were then inoculated with the test organisms, grown in their suitable broth at 37° C. for 24 hours for tested microorganisms. (1×10$^8$ CFU/ml for bacteria and 1×10$^6$ CFU/ml of yeast), each 5 ml received 0.1 ml of the above inoculum and incubated at 37° C. for 24 h. The lowest concentration showing no growth was taken as the minimum inhibitory concentration (MIC).

The results of preliminary antimicrobial testing of the target compounds, ciprofloxacin, and ketoconazole obtained using the agar well diffusion method are summarized in Tables 5 and 6. The results showed that the tested compounds demonstrated varying degrees of inhibition against the tested microorganisms. In general, strong antimicrobial activity was observed in the compounds 5a, 5b, 8a, 8c, 8f, 10a, 10c, 10d, 10e, 10f, 134a, 11c, 11d, 12b, 12c, 12d, 12e and 12f, which produced growth inhibition zones ≥25 mm against one or more of the tested microorganisms. Compounds 8e and 11b showed moderate activity with growth inhibition zones 20-25 mm, while marginal activity was exhibited by the compounds 6a, 6b, 7a, 7b, 8d, 11e, 11f and 12a (growth inhibition zones 15-19 mm). Only compound 10b has negligible effect (growth inhibition zone <15 mm) against the tested microorganisms.

The minimal inhibitory concentrations (MIC) for the active compounds (growth inhibition zones >16 mm) are summarized in Tables 7 and 8. Generally, compounds 10c, 10d, 11c, 11d, 12c, 12d, which showed highest zones of inhibition, also exhibited potent antimicrobial activity as compared to the standards against one or more of the tested microorganisms with MIC value of 125 μg/ml. Compound 10d exhibits broad-spectrum activity against all of the tested microorganisms with MIC (125 μg/mL).

The microbiological screening shows that the newly synthesized pyranocoumarins exhibit variable antimicrobial activity against gram-positive and gram-negative bacteria and yeast. Gram-positive bacteria are generally more sensitive to these compounds than are gram-negative bacteria. Compounds 8a and 8c, which contain unsubstituted benzylidene and 3,4,5-trimethoxybenzylidene, respectively, display strong antibacterial activity against gram-negative bacteria and strong-to-moderate inhibitory activity against gram-positive bacteria. Compounds 5a, 5b and 8f show strong antibacterial activity against gram-positive bacteria, with MIC values in the range 500-1000 μg/ml. Among the pyranocoumarin derivatives, compound 8a, containing unsubstituted benzylidene, possesses strong antimicrobial activity against most of the tested microorganisms relative to controls, with MIC values ranging from 250-500 μg/ml. In addition, strong antimicrobial activity was observed against *S. cerevisiae* in compounds 5a, 5b and 8c, with MIC value of 500 μg/ml.

Most of the coumarin-3-sulfonamide derivatives exhibit strong-to-moderate antimicrobial activity with respect to controls. Generally, the results show that most of the tested compounds show broad-spectrum antimicrobial activity. In addition, compounds 10a, 10c, 10d, 11a, 11c, 11d, 12c and 12d exhibit antimicrobial activity equal to or higher than the control antimicrobials against one or more of the tested microorganisms.

Compounds 10c, 10d, 11c and 11d, containing sulfadiazine and 4-hydroxyphenyl moieties, respectively, exhibit antibacterial activity higher than the control ciprofloxacin against *S. aureus*, with a MIC value of 125 μg/ml. Compounds 10a, 12c and 12d, containing sulfanilamide and 4-chlorophenyl moieties, respectively, exhibit antibacterial activity equal to ciprofloxacin against *S. aureus*, with MIC value of 250 μg/ml. The antibacterial activity against *B. subtilis* of the compounds 10c and 10d, substituted with sulfadiazine, was higher than the reference drug, while compounds 10a, 11c, 11d, 12c and 12d have comparable antibacterial activities to the standard against the same microorganism. The antibacterial activities of compounds 10c and 10d, 12c against *B. megaterium* are comparable to ciprofloxacin. Compounds 11d and 12d, containing a methyl moiety and either 4-hydroxyphenyl or 4-chlorophenyl, respectively, show higher antibacterial activity than ciprofloxacin against *E. coli*. Compounds 10c and 12c, containing a chloro moiety and either sulfadiazine or 4-chlorophenyl, respectively, have comparable antibacterial potential against *E. coli* to the control drug. Compound 11d, containing a methyl moiety and 4-hydroxyphenyl, was the only compound to exert antibacterial activity against *P. aeruginosa* higher than that of the standard drugs, while compound 12c has comparable antibacterial activity to the standard.

The antimicrobial activity against *S. cerevisiae* of compounds 10c, 10d, 11c, 11d, 12c and 12d was higher than that of the corresponding control drug, ketoconazole. In addition, compounds 10d, 11a 11e, 11d, 12c and 12d show higher antifungal activity against *C. albicans* relative to the reference drug.

TABLE 5

Antimicrobial activity of selected pyranocoumarin derivatives

| Comp. No. | Ar | Ar' | SA | BS | BM | EC | PA | SC | CA |
|---|---|---|---|---|---|---|---|---|---|
| 5a | 4-NO$_2$C$_6$H$_4$ | — | 24 | 22 | 25 | 18 | 20 | 25 | 22 |
| 5b | 2-Furyl | — | 25 | 23 | 25 | 18 | 21 | 27 | 23 |
| 6a | 4-NO$_2$C$_6$H$_4$ | — | — | 18 | 16 | 16 | 15 | — | — |
| 6b | 2-Furyl | — | 16 | — | — | 16 | 16 | 17 | 18 |
| 7a | 4-NO$_2$C$_6$H$_4$ | — | 16 | — | — | — | — | — | — |
| 7b | 2-Furyl | — | 16 | — | — | 15 | 15 | — | — |
| 8a | 4-NO$_2$C$_6$H$_4$ | C$_6$H$_5$ | 25 | 27 | 22 | 26 | 24 | 26 | 25 |
| 8c | 4-NO$_2$C$_6$H$_4$ | 3,4,5-(OCH$_3$)$_3$C$_6$H$_2$ | 23 | 23 | 24 | 24 | 25 | 27 | 24 |
| 8d | 2-Furyl | 3,4,5-(OCH$_3$)$_3$C$_6$H$_2$ | 18 | — | — | — | — | 19 | 19 |
| 8e | 4-NO$_2$C$_6$H$_4$ | 2,4-diClC$_6$H$_3$ | 16 | 16 | 16 | 15 | 15 | 22 | 20 |
| 8f | 2-Furyl | 2,4-diClC$_6$H$_3$ | 25 | 23 | 20 | 20 | 21 | 24 | 22 |
| Ciprofloxacin | | | 28 | 30 | 30 | 30 | 30 | — | — |
| Ketoconazole | | | — | — | — | — | — | 30 | 28 |

*(—): inactive (IZ < 15 mm).
SA: *S. aureus* ATCC 29213;
BS: *B. subtilis* ATCC 6633;
BM: *B. megaterium* ATCC 9885;
EC: *E. coli* ATCC 2592;
PA: *P. aeruginosa* ATCC 27953;
SC: *S. cerevisiae* -Local isolate;
CA: *C. albicans* NRRL Y-477

TABLE 6

Antimicrobial activity of selected coumarin sulfonamide derivatives

| Comp. No. | R | R'/Ar | SA | BS | BM | EC | PA | SC | CA |
|---|---|---|---|---|---|---|---|---|---|
| 10a | Cl | H | 28 | 29 | 25 | 28 | 27 | 26 | 26 |
| 10b | CH$_3$ | H | — | — | — | — | — | — | — |
| 10c | Cl | pyrimidin-2yl | 30 | 31 | 30 | 30 | 24 | 31 | 27 |

TABLE 6-continued

Antimicrobial activity of selected coumarin sulfonamide derivatives

| Comp. No. | R | R'/Ar | SA | BS | BM | EC | PA | SC | CA |
|---|---|---|---|---|---|---|---|---|---|
| 10d | CH$_3$ | pyrimidin-2yl | 30 | 31 | 30 | 28 | 25 | 32 | 30 |
| 10e | Cl | thiazol-2-yl | 23 | 25 | 25 | 20 | 22 | 20 | 23 |
| 10f | CH$_3$ | thiazol-2-yl | 24 | 27 | 27 | 23 | 24 | 26 | 24 |
| 11a | Cl | H | 26 | 28 | 29 | 25 | 26 | 28 | 29 |
| 11b | CH$_3$ | H | 20 | 19 | 24 | 18 | 17 | 19 | 20 |
| 11c | Cl | OH | 30 | 29 | 28 | 27 | 29 | 32 | 30 |
| 11d | CH$_3$ | OH | 30 | 29 | 29 | 31 | 31 | 32 | 30 |
| 11e | Cl | — | — | 15 | 16 | — | — | — | — |
| 11f | CH$_3$ | — | 16 | 15 | 15 | — | — | — | — |
| 12a | Cl | 4-NO$_2$C$_6$H$_4$ | 16 | 18 | 18 | — | — | — | — |
| 12b | CH$_3$ | 4-NO$_2$C$_6$H$_4$ | 22 | 24 | 25 | 26 | 26 | 25 | 23 |
| 12c | Cl | 4-ClC$_6$H$_4$ | 28 | 29 | 30 | 30 | 30 | 31 | 30 |
| 12d | CH$_3$ | 4-ClC$_6$H$_4$ | 28 | 29 | 29 | 38 | 29 | 32 | 30 |
| 12e | Cl | 4-MeOC$_6$H$_4$ | 23 | 21 | 20 | 21 | 21 | 29 | 23 |
| 12f | CH$_3$ | 4-MeOC$_6$H$_4$ | 25 | 25 | 26 | 26 | 28 | 26 | 24 |
| Ciprofloxacin | | | 28 | 30 | 30 | 30 | 30 | — | — |
| Ketoconazole | | | — | — | — | — | — | 30 | 28 |

*(—): inactive (IZ < 15 mm).
SA: *S. aureus* ATCC 29213;
BS: *B. subtilis* ATCC 6633;
BM: *B. megaterium* ATCC 9885;
EC: *E. coli* ATCC 2592;
PA: *P. aeruginosa* ATCC 27953;
SC: *S. cerevisiae* -Local isolate;
CA: *C. albicans* NRRL Y-477

TABLE 7

Minimal Inhibitory Concentration (MIC) for selected pyranocoumarin derivatives

| Comp. No. | SA | BS | BM | EC | PA | SC | CA |
|---|---|---|---|---|---|---|---|
| 5a | 500 | 500 | 500 | 1,000 | 500 | 500 | 500 |
| 5b | 500 | 500 | 500 | 1,000 | 1,000 | 500 | 500 |
| 6a | N.D. | 1,000 | N.D. | N.D. | N.D. | N.D. | N.D. |
| 6b | N.D. | N.D. | N.D. | N.D. | N.D. | 1,000 | 1,000 |
| 8a | 250 | 250 | 500 | 250 | 500 | 500 | 500 |
| 8c | 500 | 500 | 500 | 500 | 500 | 500 | 500 |
| 8d | 1,000 | N.D. | N.D. | N.D. | N.D. | 1,000 | 1,000 |
| 8e | N.D. | N.D. | N.D. | N.D. | N.D. | 500 | 500 |
| 8f | 500 | 500 | 1,000 | 1,000 | 1,000 | 500 | 500 |
| Ciprofloxacin | 125 | 125 | 125 | 125 | 125 | N.D. | N.D. |
| Ketoconazole | N.D. | N.D. | N.D. | N.D. | N.D. | 125 | 125 |

* N.D.: Not determined.

TABLE 8

Minimal Inhibitory Concentration (MIC) for selected coumarin sulfonamides

| Comp. No. | SA | BS | BM | EC | PA | SC | CA |
|---|---|---|---|---|---|---|---|
| 10a | 250 | 250 | 500 | 250 | 250 | 250 | 250 |
| 10c | 125 | 125 | 125 | 125 | 250 | 125 | 125 |
| 10d | 125 | 125 | 125 | 125 | 125 | 125 | 125 |
| 10e | 500 | 500 | 500 | 500 | 1000 | 1000 | 500 |
| 10f | 250 | 250 | 250 | 500 | 500 | 250 | 500 |
| 11a | 500 | 250 | 250 | 500 | 500 | 250 | 250 |
| 11b | 1000 | 1000 | 1000 | 1000 | 1000 | 1000 | 1000 |
| 11c | 125 | 125 | 250 | 250 | 250 | 125 | 125 |
| 11d | 125 | 125 | 250 | 125 | 125 | 125 | 125 |
| 12a | N.D. | 1000 | 1000 | N.D. | N.D. | N.D. | N.D. |

TABLE 8-continued

Minimal Inhibitory Concentration (MIC) for selected coumarin sulfonamides

| Comp. No. | Minimal Inhibitory Concentration (MIC, µg/ml) | | | | | | |
|---|---|---|---|---|---|---|---|
| | SA | BS | BM | EC | PA | SC | CA |
| 12b | 500 | 500 | 500 | 250 | 250 | 500 | 500 |
| 12c | 250 | 250 | 250 | 250 | 250 | 125 | 125 |
| 12d | 250 | 250 | 250 | 250 | 250 | 125 | 125 |
| 12e | 500 | 500 | 500 | 500 | 500 | 250 | 500 |
| 12f | 500 | 500 | 250 | 250 | 250 | 500 | 500 |
| Ciprofloxacin | 125 | 125 | 125 | 125 | 125 | N.D. | N.D. |
| Ketoconazole | N.D. | N.D. | N.D. | N.D. | N.D. | 125 | 125 |

* N.D.: Not determined,

Example 14

Anti-Inflammatory Activity of the Coumarin Derivatives

The newly synthesized compounds were individually tested for their in vitro anti-inflammatory activity against proteinase enzyme. In addition, compounds 5b, 6b, 10f and 11c have been tested in vivo for their acute anti-inflammatory activity using formaldehyde-induced paw oedema method in rats.

For proteinase inhibitory activity, the reaction mixture (2 ml) contained 0.06 mg trypsin, 20 mM Tris HCl buffer (pH 7.4) and 1 ml test sample (250 µg/ml for each compound). The mixture was incubated for 5 min and then 1 ml of 0.8% (w/v) casein was added. The mixture was incubated for an additional 20 min. 1 ml of 10% perchloric acid was added to arrest the reaction. The cloudy suspension was centrifuged, and the absorbance of the supernatant was read at 280 nm. Reference standard compound aspirin was used as the positive control for this assay. The experiment was performed in triplicate. Percentage inhibition of protein denaturation was calculated by using the following formula:

$$\% \text{ Inhibition} = 100 - \left[\frac{(A_{control} - A_{test})}{A_{control}} \times 100\right]$$

where $A_{control}$ is the absorbance of the control reaction and $A_{test}$ is the absorbance of the control reaction with sample.

Proteinases play a significant role in inflammatory reactions, particularly in the context of arthritic reactions. Proteinases typically are sequestered in lysosomal granules of neutrophils and provide significant protection against tissue damage and proteolytic activity of neutrophils during inflammatory reactions.

The assayed proteinase inhibitory activity of the target compounds is summarized in Tables 9 and 10. The inhibition of proteinase activity at 250 µg/ml for each compound is highest in compounds 6a and 5b, with inhibition values of 79.72±4.51% and 74.68±3.01%, respectively. Compounds 8c and 12a also have high percentage inhibition values of 68.5±6.23% and 62.14±4.87%, respectively. Compounds 6b, 8d, 8e, 10f, 11a and 11c show percentage inhibition values in the range of 41-49%. Compounds 7a, 7b, 10d and 12d show modest proteinase inhibitory activity with the percentage inhibition values in the range of 31-36%. The remaining compounds show relatively weak anti-proteinase activity with percentage inhibition values below 30%. Compound 12b, shows negligible, if any, anti-proteinase activity at the tested concentration.

The pyranocoumarins 6a, 5b, 8c and 6b showed more potent anti-proteinase activity than the control anti-inflammatory, aspirin. Meanwhile, compounds 8d and 8e were comparable to the control. The remaining compounds of this series showed moderate-to-poor anti-proteinase activity. Compound 5a, which features a 4-nitrophenyl moiety, shows weak anti-proteinase activity, while replacement of the cyano group of 5a with carboxamide (6a) significantly enhances the proteinase inhibitory activity. In addition, replacement of the protons of the amino group with 3,4,5-trimethoxybenzylidene and 2,4-dichlorobenzylidene (8c and 8e, respectively) seem to significantly enhance the proteinase inhibitory activity. This suggests that the 4-nitrophenyl alone in the pyranocoumarin does not contribute to a significant anti-proteinase activity, but its presence enhances such activity synergistically with a carboxamide, 3,4,5-trimethoxybenzylidene or 2,4-dichlorobenzylidene group. In contrast, compound 5b, containing furan-2-yl, shows significant anti-proteinase activity while hydrolysis of the cyano group to give carboxamide (6b) or replacement of protons of the amino group with 3,4,5-trimethoxybenzylidene or 2,4-dichlorobenzylidene (8d and 8f) reduces the activity by more than 25%. Compounds 7a and 7b exhibit modest anti-proteinase activity. This is likely due to the presence of N,N-dimethyl formimidamide at position 2 of the pyrano ring.

Regarding the coumarin-3-sulfonamides, only compound 12a exhibits higher anti-proteinase activity than aspirin. The presence of the chloro substituent at position 6 of the coumarin ring, along with the 4-nitrophenyl in the chalcone moiety, may contribute to this activity. Conversely, replacement of this chloro substituent with methyl diminishes the anti-proteinase activity. Compounds 10f, 11a and 11c possess comparable activity to that of aspirin. The remaining coumarin-3-sulfonamides exhibit modest-to-poor anti-proteinase activity. The presence of a methyl moiety at position 6, along with a pyrimidine or thiazole ring in compounds 10d and 10f, seems to play a strong role in their anti-proteinase activity. Replacement of the methyl moiety with a chloro moiety, or the pyrimidine or thiazole ring with hydrogen, significantly reduces the activity. Compounds 11e and 11f show poor anti-proteinase activity due to the presence of 4-acetylphenyl at position 3 of the coumarin rings. Compounds 11a and 11c have significant anti-proteinase activity that could be due to the presence of the chloro moiety and the phenyl and 4-hydroxyphenyl at positions 6 and 3, respectively, of the coumarin ring. In contrast, replacement of the chloro moiety with methyl may reduce the anti-proteinase activity significantly. Compounds 12e and 12f exhibit weak anti-proteinase activity that might be due to the presence of 4-methoxyphenyl in the chalcone moiety. Compound 12d, containing methyl and 4-chlorophenyl, shows modest anti-proteinase activity. Meanwhile, compound 12c, containing chloro and 4-chlorophenyl, exhibits poor activity.

TABLE 9

Proteinase inhibitory activity of selected pyranocoumarin derivatives

| Compound no. | Ar | Ar' | % Inhibition[a, b, c] |
|---|---|---|---|
| 5a | 4-NO$_2$C$_6$H$_4$ | — | 17.38 ± 1.63 |
| 5b | 2-Furyl | — | 74.68 ± 3.01 |
| 6a | 4-NO$_2$C$_6$H$_4$ | — | 79.72 ± 4.51 |

TABLE 9-continued

Proteinase inhibitory activity of selected pyranocoumarin derivatives

| Compound no. | Ar | Ar' | % Inhibition[a, b, c] |
|---|---|---|---|
| 6h | 2-Furyl | — | 49.28 ± 10.93 |
| 7a | 4-NO$_2$C$_6$H$_4$ | — | 31.99 ± 2.45 |
| 7b | 2-Furyl | — | 33.17 ± 2.79 |
| 8a | 4-NO$_2$C$_6$H$_4$ | C$_6$H$_5$ | N.D. |
| 8c | 4-NO$_2$C$_6$H$_4$ | 3,4,5-(OCH$_3$)$_3$C$_6$H$_2$ | 68.5 ± 6.23 |
| 8d | 2-Furyl | 3,4,5-(OCH$_3$)$_3$C$_6$H$_2$ | 43.4 ± 1.52 |
| 8e | 4-NO$_2$C$_6$H$_4$ | 2,4-diCl C$_6$H$_3$ | 45.78 ± 1.62 |
| 8f | 2-Furyl | 2,4-diCl C$_6$H$_3$ | 26.83 ± 5.33 |
| Aspirin * | | | 45.83 ± 4.21 |

[a] mean ± SD (n = 3).
[b] (—): inactive.
[c] (N.D.): Not determined.
* Positive control.

TABLE 10

Proteinase inhibitory activity of selected coumarin sulfonamide derivatives

| Compound no. | R | R'/Ar' | % Inhibition[a, b, c] |
|---|---|---|---|
| 10a | Cl | H | 18.78 ± 2.05 |
| 10b | CH$_3$ | H | 5.93 ± 2.11 |
| 10c | Cl | pyrimidin-2yl | 8.9 ± 2.04 |
| 10d | CH$_3$ | pyrimidin-2yl | 36.84 ± 4.87 |
| 10e | Cl | thiazol-2-yl | 19.8 ± 2.54 |
| 10f | CH$_3$ | thiazol-2-yl | 43.88 ± 5.6 |
| 11a | Cl | H | 44.7 ± 8.22 |
| 11b | CH$_3$ | H | 14.3 ± 2.21 |
| 11c | Cl | OH | 41.69 ± 2.83 |
| 11d | CH$_3$ | OH | 20.15 ± 7.31 |
| 11e | Cl | — | 18.5 ± 3.47 |
| 11f | CH$_3$ | — | 2.0 ± 1.4 |
| 12a | Cl | 4-NO$_2$C$_6$H$_4$ | 62.14 ± 4.87 |
| 12b | CH$_3$ | 4-NO$_2$C$_6$H$_4$ | — |
| 12c | Cl | 4-ClO$_6$H$_4$ | 17.6 ± 6.86 |
| 12d | CH$_3$ | 4-ClO$_6$H$_4$ | 31.88 ± 3.82 |
| 12e | Cl | 4-MeOC$_6$H$_4$ | 22.83 ± 4.88 |
| 12f | CH$_3$ | 4-MeOC$_6$H$_4$ | 21.7 ± 7.6 |
| Aspirin * | | | 45.83 ± 4.21 |

[a] mean ± SD (n = 3).
[b] (—): inactive.
[c] (N.D.): Not determined.
* Positive control.

Testing was performed to determine formaldehyde-induced rat paw oedema (edema). For the formaldehyde-induced rat paw oedema (edema) test, female Wister albino rats (150-175 g) were used for determination of the anti-inflammatory activities. The rats were obtained from the animal house colony of the National Organization for Drug Control and Research (NODCAR), Egypt. The animals were kept in standard plastic cages in an air conditioned room at 22±3° C., 55±5% humidity and supplied with standard laboratory diet and water ad libitum. All animal experimental procedures were carried out according to the Ethics Committee of the National Research Centre, Cairo, Egypt and followed the guidelines of the National Institutes of Health, Guide for Care and Use of Laboratory Animals (1985). The rats were classified into the following groups (6 rats each): (1) positive control group, in which paw oedema was induced by 0.2 ml (1%, w/v) of formaldehyde injected in the sub-plantar area of the right hind paw of the rat; and (2) prophylactic groups, in which all drug regimens were given one hour before induction of paw oedema, the groups including an indomethacin reference group where rats were given indomethacin orally in dose of 25 mg/kg, and test groups where rats were given coumarins 5b, 6a, 10f and 11c orally in a dose of 2.5 mg/kg each.

The percentage protection against inflammation was calculated by using following formula:

$$\% \text{ Inhibition} = \frac{(Vc - Vd)}{Vc} \times 100$$

where Vc is the mean percentage increase in paw volume in the control and Vd is the mean percentage increase in paw volume after injection of the test compound. Values were expressed as mean±standard error (S.E.). Comparisons between mean values were carried out using two-way analysis of variance (ANOVA), followed by Tukey Kramer multiple comparisons test for all acute toxicity study tests. P-value<0.0001 was considered significant. Graph pad prism software (version 6) was used to carry out all statistical tests.

Rat paw volumes were measured at 1, 2 and 3 hours after sub-plantar injection of 0.2 ml (1%, w/v) of formaldehyde as a positive control group. Formaldehyde produced significant increases in paw volumes by 109.6%, 108.7% and 94.89%, respectively, of their basal volumes (FIG. 1). Indomethacin (25 mg/kg) is used orally as a control anti-inflammatory, and produces significant inhibition of inflammation, as evidenced by reduced paw volume, when compared to the positive control group by 72.09, 74.79 and 71.5% when measured at 1, 2 and 3 hours after sub-plantar injection of 0.2 ml (1%, w/v) of formaldehyde, respectively.

Figure 2:
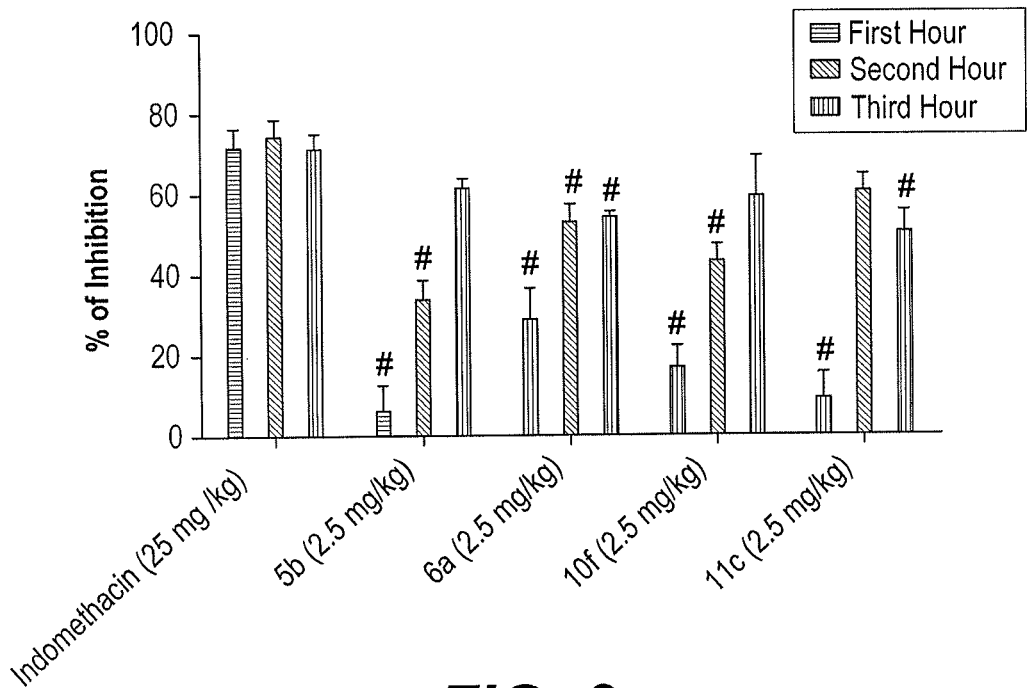
FIG. 2 is a chart reporting the percent inhibition by treatment with the control drug indomethacin (25 mg/kg) compared to compounds 5b, 6a, 10f and 11c (2.5 mg/kg), respectively, on rat paw oedema (edema) induced by formaldehyde (0.2 ml/kg).

Regarding the anti-inflammatory effect of coumarins 5b, 6a, 10f and 11c, all compounds produce significant protection against inflammation throughout the experiment duration (FIG. 2). The inhibition by compound 6a is significantly more than the others tested, showing 29.2% inhibition only one hour after induction of inflammation, but less than that of indomethacin, and using one-tenth the concentration of compounds when compared with indomethacin concentration. Compound 6a was followed by compound 10f (17.18% inhibition), 11c (9.45%) and 5b (6.57%). Moreover, the anti-inflammatory effect of the compounds was significantly increased after two and three hours when compared to the positive control group.

Example 15

Estimation of Lipophilicity

Lipophilicity is among the most important properties in drug optimization. Lipophilicity affects not only the pharmacodynamic profile of the drug, but also its pharmacokinetics.

The in silico lipophilicity values of the biologically tested compounds were calculated and expressed as consensus Log P using SwissADME web tool. Consensus Log P is the average of five different prediction methods for the calculation of computerized partition coefficient, including, ilog P, Xlog P3, Wlog P, Mlog P and Log P$_{SILICOS-IT}$.

A correlation was not observed between antioxidant or anti-inflammatory activities and in silico estimated lipophilicity for the present compounds (Tables 11 and 12). On the other hand, a correlation was observed between the antimicrobial activity and the in silico estimated lipophilicity. However, increasing the lipophilicity of compounds allows better penetration through microbial cell membranes, thereby increasing antimicrobial activity. In fact, only compound 10b was inactive against all tested microorganisms, showing the lowest consensus Log P value (1.05) amongst all the tested compounds. The lack of microbial activity of 10b could be due to the low Log P value of this compound. Meanwhile, the remaining compounds, which have mild to strong activity against one or more microorganisms, have consensus Log P values in the range of 1.23-5.33. Lipophilicity is not the only factor influencing the biological activity; other factors, such as electronic effects and steric properties, may also contribute to the biological activity of the tested compounds.

TABLE 11

Lipophilicity of selected pyranocoumarin derivatives

| Comp No. | Ar | Ar' | Consensus Log P |
|---|---|---|---|
| 5a | 4-$NO_2C_6H_4$ | — | 2.5 |
| 5b | 2-Furyl | — | 2.39 |
| 6a | 4-$NO_2C_6H_4$ | — | 1.76 |
| 6b | 2-Furyl | — | 1.75 |
| 7a | 4-$NO_2C_6H_4$ | — | 3.03 |
| 7b | 2-Furyl | — | 2.94 |
| 8a | 4-$NO_2C_6H_4$ | $C_6H_5$ | 4.29 |
| 8c | 4-$NO_2C_6H_4$ | 3,4,5-tri$MeOC_6H_2$ | 4.21 |
| 8d | 2-Furyl | 3,4,5-tri$MeOC_6H_2$ | 4.21 |
| 8e | 4-$NO_2C_6H_4$ | 2,4-di$ClC_6H_3$ | 5.33 |
| 8f | 2-Furyl | 2,4-di$ClC_6H_3$ | 5.28 |

TABLE 12

Lipophilicity of selected coumarin sulfonamide derivatives

| Comp. No. | R | R'/Ar' | Consensus Log P |
|---|---|---|---|
| 10a | Cl | H | 1.23 |
| 10b | $CH_3$ | H | 1.05 |
| 10c | Cl | pyrimidin-2yl | 1.88 |
| 10d | $CH_3$ | pyrimidin-2yl | 1.71 |
| 10e | Cl | thiazol-2-yl | 2.51 |
| 10f | $CH_3$ | thiazol-2-yl | 2.36 |
| 11a | Cl | H | 2.52 |
| 11b | $CH_3$ | H | 2.41 |
| 11c | Cl | OH | 2.03 |
| 11d | $CH_3$ | OH | 1.90 |
| 11e | Cl | — | 2.45 |
| 11f | $CH_3$ | — | 2.32 |
| 12a | Cl | 4-$NO_2C_6H_4$ | 3.5 |
| 12b | $CH_3$ | 4-$NO_2C_6H_4$ | 3.15 |
| 12c | Cl | 4-$ClO_6H_4$ | 4.48 |
| 12d | $CH_3$ | 4-$ClO_6H_4$ | 4.32 |
| 12e | Cl | 4-$MeOC_6H_4$ | 3.88 |
| 12f | $CH_3$ | 4-$MeOC_6H_4$ | 3.73 |

Example 16

Drug-Likeness Assessment

In order to assess the drug-likeness of the newly synthesized compounds, in silico Lipinski Rule of Five (RO5) and topological polar surface area (TPSA) analysis were conducted using Molinspiration, an online cheminformatics software which provide web-based interactive calculation of molecular properties like molecular weight, hydrogen bond donors as well as acceptors and calculated partition coefficient of the molecules.

It has been reported that 90% of orally active compounds that reached phase II clinical trials or higher satisfy Lipinski's rule of five. This rule states that a molecule likely to be developed as an orally active drug candidate should not show more than one violation of the following four criteria: Molecular weight: ≤500, octanol-water coefficient (Log P): ≤5, H-bond donors (n-OHNH): ≤5 and H-bond acceptors (n-ON): ≤10 (Lipinski et al., "Experimental and computational approaches to estimate solubility and permeability in drug discovery and development settings" Adv Drug Deliv Rev 23, 3-25, 1997). Despite the importance of RO5 to label a molecule as 'drug-like', these criteria are restricted to the issue of oral bioavailability via passive transport only. In addition, TPSA is another major factor for predicting oral availability of compounds, and its values for intestinal absorption showed be less than 140 Å$^2$ (Clark, 1999).

The results in Table 13 and 14 showed that all compounds have less than or equal to 4 hydrogen bond donors. The number of hydrogen bond acceptors is less than or equal to ten for all compounds except compounds 8c, 10c and 10d. The molecular weight of compounds 8c, 8e, 10c, 10e, 12a-c, 12e is shown to be more than 500 daltons. The octanol-water partition coefficient (log P) is not more than 5 for all compounds except compounds 8a, 8e, 8f, 12c and 12d. These results indicate that all compounds are capable of being developed as an orally active drug candidate except compounds 8c, 8e, 10c, 12c and 12e, which violate the RO5 criteria. However, some drugs in clinical use do not obey the RO5 criteria. The TPSA is less than 140 Å$^2$ in all compounds except 6a, 10a-f, 12a and 12b, which indicates likely easy permeability through the intestinal cell membrane. Based on these findings and the results of the biological tests, all tested compounds followed the in silico criteria for an orally active drug. In light of the demonstrated biological activities above, the compounds are particularly suited for use as orally active agents.

TABLE 13

Lipinski parameters and TPSA of selected pyranocoumarin derivatives

| Comp. No. | Mol. Wt. | miLogP | n-ON | n-OHNH | RO5 violations | TPSA (Å$^2$) |
|---|---|---|---|---|---|---|
| Rule | ≤500 | ≤5 | ≤10 | ≤5 | ≤1 | ≤140 |
| 5a | 375.34 | 3.10 | 8 | 2 | 0 | 135.08 |
| 5b | 320.30 | 2.40 | 6 | 2 | 0 | 102.40 |
| 6a | 393.36 | 2.05 | 9 | 4 | 0 | 154.39 |
| 6b | 338.32 | 1.35 | 7 | 4 | 0 | 121.70 |
| 7a | 430.42 | 3.58 | 9 | 0 | 0 | 124.66 |
| 7b | 375.38 | 2.88 | 7 | 0 | 0 | 91.98 |
| 8a | 463.45 | 5.16 | 8 | 0 | 1 | 121.42 |
| 8b | 408.41 | 4.45 | 6 | 0 | 0 | 88.74 |
| 8c | 553.53 | 4.79 | 11 | 0 | 2 | 149.13 |
| 8d | 498.49 | 4.08 | 9 | 0 | 0 | 116.44 |
| 8e | 532.34 | 6.44 | 8 | 0 | 2 | 121.42 |
| 8f | 477.30 | 5.74 | 6 | 0 | 1 | 88.74 |

TABLE 14

Lipinski parameters and TPSA of selected coumarin sulfonamide derivatives

| Comp. No. | Mol.Wt. | miLogP | n-ON | n-OHNH | RO5 violations | TPSA (Å$^2$) |
|---|---|---|---|---|---|---|
| Rule | ≤500 | ≤5 | ≤10 | ≤5 | ≤1 | ≤140 |
| 10a | 430.85 | 1.76 | 9 | 4 | 0 | 156.77 |
| 10b | 410.43 | 1.53 | 9 | 4 | 0 | 156.77 |
| 10c | 508.92 | 2.01 | 11 | 2 | 2 | 168.56 |
| 10d | 488.50 | 1.78 | 11 | 3 | 1 | 168.56 |
| 10e | 513.96 | 2.89 | 10 | 3 | 1 | 155.67 |
| 10f | 493.54 | 2.66 | 10 | 3 | 0 | 155.67 |
| 11a | 351.77 | 3.07 | 6 | 2 | 0 | 96.61 |
| 11b | 331.35 | 2.84 | 6 | 2 | 0 | 96.61 |
| 11c | 367.77 | 2.59 | 7 | 3 | 0 | 116.84 |

TABLE 14-continued

Lipinski parameters and TPSA of selected coumarin sulfonamide derivatives

| Comp. No. | Mol.Wt. | miLogP | n-ON | n-OHNH | RO5 violations | TPSA (Å$^2$) |
|---|---|---|---|---|---|---|
| 11d | 347.35 | 2.36 | 7 | 3 | 0 | 116.84 |
| 11e | 393.80 | 2.97 | 7 | 2 | 0 | 113.68 |
| 11f | 373.39 | 2.74 | 7 | 2 | 0 | 113.68 |
| 12a | 526.91 | 4.90 | 10 | 2 | 1 | 159.50 |
| 12b | 506.49 | 4.67 | 10 | 2 | 1 | 159.50 |
| 12c | 516.36 | 5.62 | 7 | 2 | 2 | 113.68 |
| 12d | 495.94 | 5.39 | 7 | 2 | 1 | 113.68 |
| 12e | 511.94 | 5.00 | 8 | 2 | 2 | 122.91 |
| 12f | 491.52 | 4.77 | 8 | 2 | 0 | 122.91 |

It is to be understood that the coumarin derivatives are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A pyranocoumarin compound of formula 2:

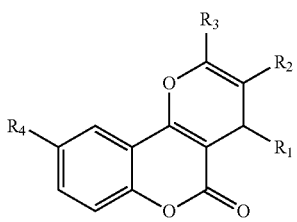

wherein $R_1$ is 4-NO$_2$C$_6$H$_4$ or 2-Furyl; $R_2$ is CN or CONH$_2$; $R_3$ is NH$_2$, NCHN(CH$_3$)$_2$, or NCHR$_6$; $R_4$ is Cl or CH$_3$; $R_6$ is C$_6$H$_5$, 3,4,5-(CH$_3$O)$_3$C$_6$H$_2$ or 2,4-Cl$_2$C$_6$H$_3$; or a pharmaceutically acceptable salt thereof; with the proviso that 2-amino-9-methyl-4-(4-nitrophenyl)-5-oxo-4H,5H-pyrano[3,2-c][1]benzopyran-3-carbonitrile is excluded.

2. The pyranocoumarin compound according to claim 1 wherein the compound has a formula selected from the group consisting of:

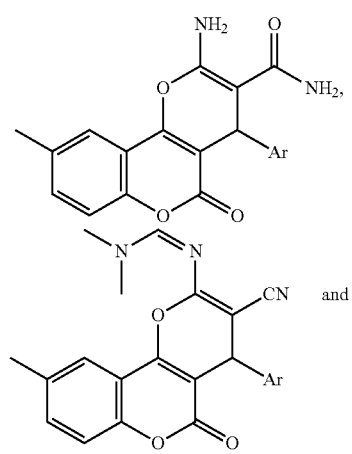

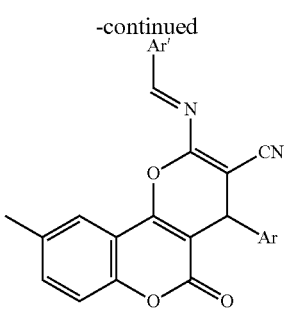

wherein Ar is selected from a group consisting of 4-NO$_2$C$_6$H$_4$ and 2-Furyl; and Ar' is selected from the group consisting of C$_6$H$_5$, 3,4,5-triMeOC$_6$H$_2$ and 2,4-Cl$_2$C$_6$H$_3$.

3. A pharmaceutical composition comprising:
the compound of claim 1 and a pharmaceutically acceptable carrier.

4. The pharmaceutical composition of claim 3, wherein the pharmaceutical composition is in a unit dosage form.

5. The pharmaceutical composition of claim 4, wherein the unit dosage form is a tablet, pill, capsule, granule, powder, ointment, sterile parenteral solution or suspension, metered aerosol or liquid spray, drops, ampule, injection, teaspoonful, or suppository.

6. A method for achieving an effect in a patient, comprising the step of administering an effective amount of the compound or a pharmaceutically acceptable salt thereof according to claim 1 to the patient, wherein the effect is an antioxidant effect, an antimicrobial effect, or an anti-inflammatory effect.

7. A method of reducing one or more conditions of an inflammatory response, a microbial infection and oxidative stress in a patient experiencing one or more of said conditions, comprising the step of administering to the patient a therapeutically effective amount of the pharmaceutical composition according to claim 3.

8. The method of claim 7, wherein the composition is administered orally, nasally, rectally, parenterally, intracisternally, intravaginally, intraperitoneally, topically, transdermally, or by surgical implantation.

9. The method of claim 7, wherein the composition is administered in a form selected from the group consisting of liquid oral preparation, solid oral preparation, parenteral preparation, injectable suspension, and liposome.

10. A method of making the compound of claim 1, comprising the steps of:
mixing a 2-amino-9-methyl-5-oxo-4-aryl-4H,5H-pyrano[3,2-c]chromene-3-carbonitrile with sulfuric acid at room temperature to form a precipitate; and
isolating the precipitate.

11. A method of making the compound of claim 1, comprising the steps of:
refluxing a 2-amino-9-methyl-5-oxo-4-aryl-4H,5H-pyrano[3,2-c]chromene-3-carbonitrile with DMF-DMA to form a precipitate; and
isolating the precipitate.

12. A method of making the compound of claim 1, comprising the steps of:
mixing a 2-amino-9-methyl-5-oxo-4-aryl-4H,5H-pyrano[3,2-c]chromene-3-carbonitrile with an aromatic aldehyde selected from the group consisting of benzaldehyde, 2,4-dichlorobenzaldehyde and 2,3,4-trimethoxybenzaldehyde in 1,4 dioxane solvent to form a mixture;
irradiating the mixture in a microwave device; and evaporating the solvent from the irradiated mixture to leave a residue; and isolating the residue.

13. A method of making a pharmaceutical composition according to claim 3, comprising the steps of:

mixing the compound under sterile conditions with the pharmaceutically acceptable carrier to form a mixture; and providing the mixture in a unit dosage form.

14. A coumarin sulfonamide compound of formula 3:

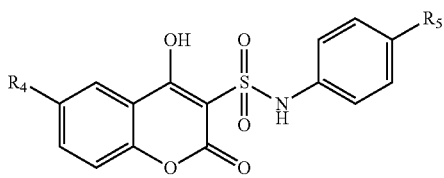

wherein $R_4$ is Cl or $CH_3$; $R_5$ is $SO_2NHR_7$, H, OH, $COCH_3$ or $COC_2H_2R_8$; $R_7$ is H, 1,3-thiazole, or 1,3-diazine; and $R_8$ is $4-O_2NC_6H_4$, $4-CH_3OC_6H_4$, or $4-ClC_6H_4$; or a pharmaceutically acceptable salt thereof.

15. The coumarin sulfonamide compound according to claim 14 wherein the compound has a formula selected from the group consisting of:

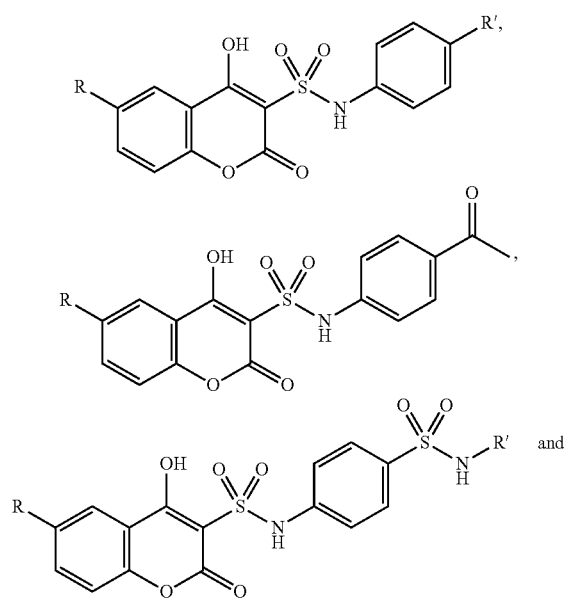

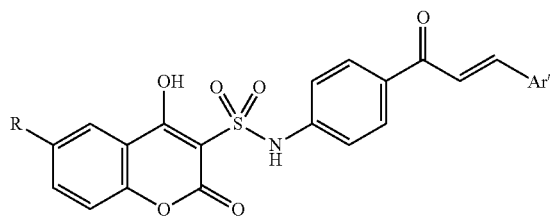

wherein R is Cl or $CH_3$; R' is H, 1,3-diazine-2-yl, 1,3-thiazol-2-yl, $COCH_3$, or OH; and Ar' is $4-NO_2C_6H_4$, $4-ClC_6H_4$ or $4-MeOC_6H_4$.

16. A pharmaceutical composition comprising:

the coumarin compound of claim 14 with a pharmaceutically acceptable carrier.

17. A method of making the compound of claim 14, comprising the steps of:

adding chlorosulfonic acid to one of 6-chloro-4-hydroxycoumarin or 4-hydroxy-6-methylcoumarin in dichloromethane at near 0° C. to form a precipitate; and isolating the precipitate as an intermediate product.

18. The method of claim 17, further comprising the steps of:

refluxing the intermediate product with a compound selected from the group consisting of sulfanilamide, sulfadiazine and sulfathiazole in EtOH solvent to produce a second precipitate; and isolating the second precipitate.

19. The method of claim 17, further comprising the steps of:

refluxing the intermediate product with a compound selected from the group consisting of aniline, 4-hydroxyaniline and 4-acetylaniline in EtOH to produce a second precipitate; and isolating the second precipitate.

20. The method of claim 19, further comprising the steps of:

dissolving the second precipitate and 4-nitrobenzaldehyde, 4-chlorobenzaldehyde or 4-methoxybenzaldehyde in EtOH to form a solution;

adding sodium hydroxide to the solution and mixing to produce a third precipitate; and isolating the third precipitate.

* * * * *